(12) United States Patent
Covalin et al.

(10) Patent No.: US 8,257,684 B2
(45) Date of Patent: Sep. 4, 2012

(54) METHODS FOR IDENTIFYING AND TARGETING AUTONOMIC BRAIN REGIONS

(75) Inventors: Alejandro Covalin, Los Angeles, CA (US); Antonio Afonso Ferreira De Salles, Los Angeles, CA (US)

(73) Assignee: Neurosigma, Inc., Los Angeles, CA (US)

( * ) Notice: Subject to any disclaimer, the term of this patent is extended or adjusted under 35 U.S.C. 154(b) by 545 days.

(21) Appl. No.: 12/411,710

(22) Filed: Mar. 26, 2009

(65) Prior Publication Data

US 2009/0246140 A1 Oct. 1, 2009

Related U.S. Application Data

(63) Continuation of application No. 61/039,671, filed on Mar. 26, 2008.

(51) Int. Cl.
*A61K 51/00* (2006.01)
*A61M 36/14* (2006.01)

(52) U.S. Cl. ............. 424/1.89; 424/1.11; 424/1.65; 424/1.81; 424/1.85

(58) Field of Classification Search ............ 424/1.11, 424/1.49, 1.65, 1.73, 1.81, 1.85, 1.89, 9.1, 424/9.2, 9.3, 9.4, 9.5, 9.6, 9.7, 9.8
See application file for complete search history.

(56) References Cited

U.S. PATENT DOCUMENTS

| | | |
|---|---|---|
| 4,778,785 A | 10/1988 | Kochi et al. |
| 5,055,479 A | 10/1991 | Takiguchi et al. |
| 5,264,208 A | 11/1993 | Hughes, Jr. et al. |
| 5,782,798 A | 7/1998 | Rise |
| 5,834,192 A | 11/1998 | Akerblom et al. |
| 6,129,685 A | 10/2000 | Howard, III |
| 6,587,719 B1 | 7/2003 | Barrett et al. |
| 6,611,715 B1 | 8/2003 | Boyeja |
| 6,950,707 B2 | 9/2005 | Whitehurst |
| 7,345,144 B2 | 3/2008 | Sharma et al. |
| 7,365,070 B2 | 4/2008 | Vos et al. |
| 7,493,171 B1 | 2/2009 | Whitehurst et al. |
| 2002/0165363 A1 | 11/2002 | Sato et al. |
| 2003/0113263 A1 | 6/2003 | Marks et al. |
| 2003/0138424 A1 | 7/2003 | Sato et al. |
| 2004/0147746 A1 | 7/2004 | Vos et al. |
| 2006/0293223 A1 | 12/2006 | Gadski et al. |
| 2007/0149465 A1 | 6/2007 | Kenley et al. |
| 2007/0293498 A1 | 12/2007 | Vos et al. |
| 2008/0046012 A1 | 2/2008 | Covalin et al. |
| 2008/0241287 A9 | 10/2008 | Rosenbloom |

FOREIGN PATENT DOCUMENTS

| WO | WO 2003/031410 A1 | 4/2003 |
|---|---|---|
| WO | WO 2004/050610 A2 | 6/2004 |

OTHER PUBLICATIONS

Horvath et al (The Journal of Neuroscience, Feb. 1999, vol. 19, No. 3, pp. 1072-1087).*

Ashford, Michael L. et al., "Glucose-induced excitation of hypothalamic neurones is mediated by ATP-sensitive K+ channels", *Pflugers Arch* 415 1990, 479-483.

Baskin, Denis G. et al., "Leptin Receptor Long-form Splice-variant Protein Expression in Neron Cell Bodies of the Brain and Co-localization with Neuropeptide Y mRNA in the Arcuate Nucleus", *J. Histochem Cytochem* 47 1999, 353-362.

Bayer, Laurence et al., "Alteration of expression of the hypocretin (orexin) gene by 2-deoxyglucose in the rat lateral hypothalamic area", *NeuroReport* 11 2000, 531-533.

Broadwell, Richard et al., "Entry of Peroxidase into Neurons of the Central and Peripheral Nervous Systems from Extracerebral and Cerebral Blood", *J Comp Neur* 166(3) 1976, 257-284.

Broberger, Christian et al., "The neuropeptide Y/agouti gene-related protein (AGRP) brain circuitry in normal, anorectic, and monosodium glutamate-treated mice", *Proc Natl Acad Sci USA* 95 1998, 15043-15048.

Burdakov, Denis et al., "Orexin Excites GABAergic Neurons of the Arcuate Nucleus by Activating the Sodium-Calcium Exchanger", *J. Neuroscience* 23(12) 2003, 4951-4957.

Castaneda, Tamara R. et al., "Symposium: Ghrelin: Its Role in Energy Balance, Obesity and the Neuroendocrine Control of Energy Homeostasis: The Role of Spontaneous Locomotor Activity", *J Nutr* 135 2005, 1314-1319.

Chemelli, Richard M. et al., "Narcolepsy in orexin Knockout Mice: Molecular Genetics of Sleep Regulation", *Cell* vol. 98 1999, 437-451.

De Lecea, L et al., "The hypocretins: Hypothalamus-specific peptides with neuroexcitatory activity", *Proc Natl Acad Sci USA* 95 1998, 322-327.

Defalco, Jeff et al., "Virus-assisted Mapping of Neural Inputs to a Feeding Center in the Hypothalamus", *Science* 291 2001, 2608-2613.

Dunn-Meynell, Ambrose A. et al., "Low-affinity sulfonylurea binding sites reside on neuronal cell bodies in the brain", *Brain Research* 745 1997, 1-9.

Elias, Carol F. et al., "Leptin Activates Hypothalamic CART Neurons Projecting to the Spinal Cord", *Neuron* vol. 21 1998, 1375-1385.

Elias, Carol F. et al., "Leptin Differentially Regulates NPY and POMC Neurons Projecting to the Lateral Hypothalamic Area", *Neuron* 23 1999, 775-786.

Fulwiler, Carl E. et al., "Cholecystokinin-Immunoreactive Innervation of the Ventromedial Hypothalamus in the Rat: Possible Substrate for Autonomic Regulation of Feeding", *Neuroscience Letters* 53 1985, 289-296.

Hahn, Tina M. et al., "Coexpression of Agrp and NPY in fasting-activated hypothalamic neurons", *nature neuroscience* 1 (4) 1998, 271-272.

Hakansson, M.-L. et al., "Leptin Receptor- and STAT3-Immunoreactivities in Hypocretin/Orexin Neurones of the Lateral Hypothalamus", *J. Neuroendocrinology* 11 1999, 653-663.

(Continued)

*Primary Examiner* — D L Jones
(74) *Attorney, Agent, or Firm* — Dorsey & Whitney LLP

(57) ABSTRACT

Disclosed herein are methods for identifying and targeting autonomic and autonomic-related brain regions. In one embodiment, a method of identifying a brain region in a patient comprises administering to the patient a targeting agent that activates or inhibits a brain region and imaging the brain region.

26 Claims, 1 Drawing Sheet

OTHER PUBLICATIONS

Haynes, Andrea C. et al., "Effects of single and chronic intracerebroventricular administration of the orexins on feeding in the rat", *Peptides* 20 1999, 1099-1105.

Kopell, Brian H. et al., "Neuromodulation Surgery for Psychiatric Disorders", *emedicine from WebMD* http://emedicine.medscape.com/article/1343677—overview 2008, 23 pages.

Kristensen, Peter et al., "Hypothalamic CART is a new anorectic peptide regulated by leptin", *Nature* 393 1998, 72-76.

Kruk, Menno R., "Ethology and Pharmacology of Hypothalamic Aggression in the Rat", *NeuroScience & Biobehavioral Reviews* 15 1991, 527-538.

Laviano, Alessandro et al., "Neural control of the anorexia-cachexia syndrome", *Am J Physiol Endocrinol Metab* 295 2008, E1000-E1008.

Lund, Per-Eric et al., "The Orexin OX1 Receptor Activates a Novel Ca2+ Influx Pathway Necessary for Coupling to Phospholipase C*", *J. Biol Chem* 275 (40) 2000, 30806-30812.

Muroya, Shinji et al., "Glucose-sensitive neurons in the rat arcuate nucleus contain neuropeptide Y", *Neuroscience Letters* 264 1999, 113-116.

Narita, K et al., "Subthalamic locomotor region is involved in running activity originating in the rat ventromedial hypothalamus", *Behav Brain Research* 134 2002, 275-281.

Nishimura, Hiroyuki et al., "Effects of Hypothalamic Stimulation on Activity of Dorsomedial Medulla Neurons That Respond to Subdiaphragmatic Vagal Stimulation", *J Neurophysiology* 58(4) 1987, 655-675.

Peyron, Christelle et al., "Neurons Containing Hypocretin (Orexin) Project to Multiple Neuronal Systems", *J Neuroscience* 18(23) 1998, 9996-10015.

Shakurai, Takeshi et al., "Orexins and Orexin Receptors: A Family of Hypothalamic Neuropeptices and G Protein-Coupled Receptors that Regulate Feeding Behavior", *Cell* 92 1998, 573-585.

Shioda, Sheiji et al., "Immunohistochemical localization of leptin receptor in the rat brain", *Neuroscience Letters* 243 1998, 41-44.

Shiraishi, Takemasa et al., "Effects of leptin and orexin-A on food intake and feeding related hypothalamic nerons", *Physiology & Behavior* 71 2000, 251-261.

Suzuki, Ryusuke et al., "Orexin-1 receptor immunoreactivity in chemically identified target neurons in the rat hypothalamus", *Neuroscience Letters* 324 2002, 5-8.

Thompson, R.H. et al., "Organization of inputs to the dorsomedial nucleus of the hypothalamus: a reexamination with Fluorogold and PHAL in the rat", *Brain Research Reviews* 27 1998, 89-118.

Thornhill, J.A. et al., "Electrical stimulation of the posterior and ventromedial hypothalamic nuclei causes specific activation of shivering and nonshivering thermogenesis", *Can J Physiol Pharmacol* 72 1994, 89-96.

Thornhill, J et al., "Intrascapular brown adipose tissue (IBAT) temperature and blood flow responses following ventromedial hypothalamic stimulation to sham and IBAT-denerverated rats", *Brain Research* 615 1993, 289-294.

Wang, Jian et al., "Central insulin inhibits hypothalamic galanin and neuropeptide Y gene expression and peptide release in intact rats", *Brain Research* 777 1997, 231-236.

Woods, Stephen C., "Gastrointestinal Satiety Signals, I. An overview of gastrointestinal signals that influence food intake", *Am J Physiol Gastrointest Liver Physiol* 286 2004, G7-G13.

Yamada, Hiroto et al., "Inhibition of Food Intake by Central Injection of Anti-orexin Antibody in Fasted Rats", *Biochemical and Biophysical Research Communications* 267 2000, 527-531.

Zhang, Xeuguo et al., "Stimulation of the paraventricular nucleus modulates the activity of gut-sensitive neurons in the vagal complex", *Am J. Physiol Gastrointest Liver Physiol* 277 1999, 79-90.

Author Unknown, American Cancer Society, "Cancer Facts & Figures 2008." American Cancer Society (2008).

Author Unknown, "University of Cincinnati researchers seek improved targeting in Parkinson's surgery," University of Cincinnati: pp. 1-2, (Jan. 2009).

Baker, et al., "Sexual Receptivity and Ovulation in the Cyclic Rate Involves Protein-Synthesis in the Ventromedial Hypothalamus (Vmh) and Medial Preoptic Area (Mpoa) During Late Diestrus-li," Anatomical Record, vol. 199, No. 3, p. A16 (1981).

Bernardis, et al., "The dorsomedial hypothalamic nucleus revisited: 1998 update," Proceedings of Society for Experimental Biology and Medicine, vol. 218, No. 4, pp. 284-306 (1998).

Broberger, et al., "Subtypes Y1 and Y2 of the neuropeptide Y receptor are respectively expressed in pro-opiomelanocortin-and neuropeptide-Y containing neurons of the rat hypothalamic arcuate nucleus," Neuroendocrinology, vol. 66, No. 6, pp. 393-408 (1997).

Broberger, et al., "Hypothalamic and vagal neuropeptide circuitries regulating food intake," Physiology & Behavior, vol. 74, No. 4-5, pp. 669-682 (2001).

Cowley et al., "The distribution and mechanism of action of ghrelin in the CNS demonstrates a novel hypothalamic circuit regulating energy homeostasis," Neuron, vol. 37, No. 4, pp. 649-661 (2003).

DeSalles, et al., "Functional Neurosurgery in the MRI Environment." Minim Invasive Neurosurg. 47(5): 284-289 (Oct. 2004).

DeSalles, et al., "Radiosurgery from the Brain to the Spine: 20 years experience," Acta Neurochir Suppl. 2008.101: 163-8 (2008).

Elmquist, "Anatomic basis of leptin action in the hypothalamus," Neuroendocrinology of Leptin, vol. 26, pp. 21-41 (2000).

Fadel, et al., "Anatomical Substrates of Orexin-Dopamine Interactions: Lateral Hypothalamic Projections to the Ventral Tegmental Area," Neuroscience, vol. 111, No. 2, pp. 379-387; p. 379, col. 2, para 1, p. 385, col. 1 para 2. (2002).

Fan, et al., "Cholecystokinin-mediated suppression of feeding involves the brainstem melanocortin system." Nat. Neurosci. 7, 335-336 (2004).

Foster, et al., MC4 receptor antagonists: A potential treatment for cachexia, Idrugs, vol. 8, No. 4, pp. 314-319, (2005).

Guan et al., "Evidence of altered hypothalamic pro-piomelanocortin neuropeptide Y mRNA expression in tubby mice," Molecular Brain Research, vol. 59, No. 2, pp. 273-279 (1998).

Guan, et al., "Orexinergic innervation of POMC-containing neurons in the rat arcuate nucleus," Neuroreport, vol. 12, No. 3, pp. 547-551 (2001).

Hoge, et al., "Linear Coupling Between Cerebral Blood Flow and Oxygen Consumption in Activated Human Cortex," PNAS, vol. 96, pp. 9403-9408, abstract, p. 9407, col. 2, para 4 to p. 9408, col. 1, para 2 (1999).

Horvath, et al., "Synaptic interaction between hypocretin (Orexin) and neuropeptide Y cells in the rodent and primate hypothalamus: A novel circuit implicated in metabolic and endocrine regulations," Journal of Neuroscience, vol. 19, No. 3, pp. 1072-1087 (1999).

Iversen, "Canabis and the Brain," Brain, vol. 126, pp. 1252-1270; p. 1254, col. 2, para 1; pp. 1257, col. 2, para 3, p. 1260, col. 1, para 1, 3 (2003).

Laviano, et al., "NPY and brain monoamines in the pathogenesis of cancer anorexia," Nutrition, vol. 24, No. 9, pp. 802-805 (2008).

Lin et al., "The sleep disorder canine narcolepsy is caused by a mutation in the hypocretin (orexin) receptor 2 gene," Cell, vol. 98, No. 3, pp. 365-376 (1999).

Marks, et al., "Differential role of melanocortin receptor subtypes in cachexia." Endocrinology 144, 1513-1523 (2003).

Matsuda, et al., "Altered Hypothalamic Function in Response to Glucose Ingestion in Obese Humans," Diabetes, vol. 48, pp. 1801-1806; Abstract, Fig. 1A-B; p. 1802, col. 1, para 1-2, p. 1802, col. 2, para. 3 (1999).

Mercer, et al., "Coexpression of leptin receptor and preproneuropeptide Y mRNA in arcuate nucleus of mouse hypothalamus," Journal of Neuroendocrinology, vol. 8, No. 10, pp. 733-735 (1996).

Murphy, E.J., "Stable isotope methods for the in vivo measurement of lipogenesis and triglyceride metabolism." J Anim. Sci. 84 Suppl, E94-104 (2006).

Schubert, et al., "Cancer chemoprevention by the antioxidant tempol in Atm-deficient mice." Human Molecular Genetics 13, 1793-1802 (2004).

Shannon, R.V., "A Model of Safe Levels for Electrical-Stimulation." IEEE Transactions on Biomedical Engineering 39, 424-426 (1992).

Tataranni, P.A., "Mechanisms of Weight Gain in Humans," European Review for Medical and Pharmacological Sciences, vol. 4, pp. 1-7, p. 5, col. 1, para 2, p. 5, col. 2, para 1 (2000).

Temel, et al., "Deep Brain Stimulation of the Thalamus Can Influence Penile Erection," International Journal of Impotence Research, vol. 16, pp. 91-94, p. 92, col. 2, para 4 to p. 93, col. 2, para 1 (2004).

Terhorst, G., et al., "Phaseolus-Vulgaris Leuco-Agglutinin Tracing of Intrahypothalamic Connections of the Lateral, Ventromedial, Dorsomedial md Paraventricular Hypothalamic Nuclei in the Rat,"Brain Research Bulletin, vol. 18, No. 2, pp. 191-203 (1987).

Viswanadha, et al., "Optimized conditions for measuring lipolysis in murine primary adipocytes." J Lipid Res. 47, 1859-1864 (2006).

Yee, et al., Magnetic Resonance Imaging, 20, pp. 17-26 (2002).

Zhao et al., "Comparison of TCA and ICA Techniques in fMRI Data Processing," Journal of Magnetic Resonance Imaging, vol. 19, pp. 397-402, abstract, p. 398, col. 1, para 5 to p. 398, col. 2, para 2, p. 401, col. 1, para 2 (2004).

Bagnol, Didier, "G-protein-coupled receptors in hypothalamic circuits involved in metabolic diseases," *Current Opinion in Drug Discovery & Development* 7(5) 2004, 665-682.

Benabid, Alim L. et al., "Mechanisms of Deep Brain Stimulation," *Movement Disorders* 17(3) 2002, 73-74.

Berthoud, Hans-Rudolf, "Multiple neural systems controlling food intake and body weight," *Neuroscience and Biobehavioral Reviews* 26 2002, 393-428.

Brito, Marcia N. et al., "Differential Activation of the Sympathetic Innervation of Adipose Tissues by Melanocortin Receptor Stimulation," *Endocrinology* 148(11) 2007, 5339-5347.

Canteras, N.S. et al., "Organization of Projections From the Ventromedial Nucleus of the Hypothalamus: A *Phaseolus vulgaris*-Leucoagglutinin Study in the Rat," *The Journal of Comparative Neurology* 348 1994, 41-79.

Covalin, Alejandro et al., "Deep Brain Stimulation for Obesity Control: Analyzing Stimulation Parameters to Modulate Energy Expenditure," Conference on Neural Engineering, Arlington, VA, Mar. 16-19, 2005.

Covalin-Sharfman, Alejandro, "Deep Brain Stimulation to Modulate Energy Expenditure and Neurotrophic Factors," A Dissertation, University of California, Los Angeles, 2006.

Cowley, Michael A. et al., "Integration of NPY, AGRP, and Melanocortin Signals in the Hypothalamic Paraventricular Nucleus: Evidence of a Cellular Basis for the Adipostat," *Neuron* 24 1999, 155-163.

Cowley, Michael A. et al., "Leptin activates anorexigenic POMC neurons through a neural network in the arcuate nucleus," *Nature* 411 2001, 480-484.

Cummings, David E. et al., "Melanocortins and body weight: a tale of two receptors," *nature genetics* 26 2000, 8-9.

Elmquist, Joel K. et al., "Leptin activates distinct projections from the dorsomedial and ventromedial hypothalamic nuclei," *Proc. Natl. Acad. Sci. USA* 95 1998, 741-746.

Evans, William J. et al., "Cachexia: A new definition," *Clinical Nutrition* 27 2008, 793-799.

Flanagan, Loretta M. et al., "Gastric motility in conscious rats given oxytocin and an oxytocin antagonist centrally," *Brain Research* 578 1992, 256-260.

Foster, Alan C. et al., "Melenocortin-4 Receptor Antagonists as Potential Therapeutics in the Treatment of Cachexia," *Current Topics in Medicinal Chemistry* 7 2007, 1131-1136.

Hamani, Clement, et al., "Memory Enhancement Induced by Hypothalamic/Fornix Deep Brain Stimulation," *Annals of Neurology* 63 2008, 119-123.

Harnack, Daniel et al., "The effects of electrode material, charge density and stimulation duration on the safety of high-frequency stimulation of the subthalamic nucleus in rats," *Journal of Neuroscience Methods* 138 2004, 207-216.

Hotz, Hubert G. et al., "An Improved Clinical Model of Orthotopic Pancreatic Cancer in Immunocompetent Lewis Rats," *Pancreas* 22(2) 2001, 113-121.

Inui, Akio, Cancer Anorexia-Cachexia Syndrome: Current Issues in Research and Management, *A Cancer Journal for Clinicians* 52 2002, 72-91.

Jobst, Erin E. et al., "The electrophysiology of feeding circuits," *Trends in Endocrinology and Metabolism* 15(10) 2004, 488-499.

Joppa, M.A. et al., "Central infusion of the melanocortin receptor antagonist agouti-related peptide (AgRP(83-132)) prevents cachexia-related symptoms induced by radiation and colon-26 tumors in mice," *Peptides* 28 2007, 636-642.

Kennedy, Adele et al., "The Metabolic Significance of Leptin in Humans: Gender-Based Differences in Relationship to Adiposity, Insulin Sensitivity, and Energy Expenditure," *Journal of Clinical Endocrinology and Metabolism* 82(4) 1997, 1293-1300.

Lacan, Goran et al., "Modulation of food intake following deep brain stimulation of the ventromedial hypothalamus in the vervet monkey," *J. Neurosurg.* 108 2008, 336-342.

Laviano, Alessandro et al., "NPY and brain monoamines in the pathogenesis of cancer anorexia," *Nutrition* 24 2008, 802-805.

MacDonald, Neil et al., "Understanding and Managing Cancer Cachexia," *Palliative Care* 197(1) 2003, 143-161.

Markison, Stacy et al., "The Regulation of Feeding and Metabolic Rate and the Prevention of Murine Cancer Cachexia with a Small-Molecule Melanocortin-4 Receptor Antagonist," *Endocrinology* 146(6) 2005, 2766-2773.

Mayberg Helen S. et al., "Deep Brain Stimulation for Treatment-Resistant Depression," *Neuron* 45 2005, 651-660.

McIntyre, Cameron C., "Finite Element Analysis of the Current-Density and Electric Field Generated by Metal Microelectrodes," *Annals of Biomedical Engineering* 29 2001, 227-235.

Morley, John E. et al., "Cachexia: pathophysiology and clinical relevance," *The American Journal of Clinical Nutrition* 83 2006, 735-743.

Muscaritoli, Maurizio et al., "Prevention and treatment of cancer cachexia: New insights into an old problem," *European Journal of Cancer* 42 2006, 31-41.

Plumb, J.A. et al., "Energy expenditure and protein synthesis rates in an animal model of cancer cachexia," *Clinical Nutrition* 10 1991, 23-29.

Ruffin, Marie-Pierre et al., "Electrical stimulation of the ventromedial hypothalamus enhances both fat utilization and metabolic rate that precede and parallel the inhibition of feeding behavior," *Brain Research* 846 1999, 23-29.

Schwartz, Michael W. et al., "Central nervous system control of food intake," *Nature* 404 2000, 661-671.

Sedrak, M. et al., "The role of modern imagine modalities on deep brain stimulation targeting for mental illness," *Acta Neurochir Suppl* 101 2008, 3-7.

Shimazu, T., "Central Nervous System Regulation of Liver and Adipose Tissue Metabolism," *Diabetologia* 20 1981, 343-356.

Sternson, Scott M. et al., "Topographic mapping of VMH → arcuate nucleus microcircuits and their reorganization by fasting," *Nature Neuroscience* 8(10) 2005, 1356-1363.

Takahashi, Akira et al., "Hypothalamic Regulation of Lipid Metabolism in the Rat: Effect of Hypothalamic Stimulation on Lipolysis," *Journal of the Autonomic Nervous System* 4 1981, 195-205.

Tyler, William J. et al., "Remote Excitation of Neuronal Circuits Using Low-Intensity, Low-Frequency Ultrasound," *PLoS ONE* 3(10) 2008, 1-11.

Vissing, J. et al., "Ventromedial hypothalamic regulation of hormonal and metabolic responses to exercise," *The American Journal of Physiology—Regulatory, Integrative and Comparative Physiology* 256 1989, 1019-1026.

Wikberg, Jarl E. et al., "Targeting melanocortin receptors: an approach to treat weight disorders and sexual dysfunction," *Nature Reviews Drug Discovery* (published online) 2008, 1-17.

Williams, Gareth et al., "The hypothalamus and the control of energy homeostasis, Different circuits, different purposes," *Physiology & Behavior* 74 2001, 683-701.

Wynne, Katie et al., "Appetite control," *Journal of Endocrinology* 184 2005, 291-318.

\* cited by examiner

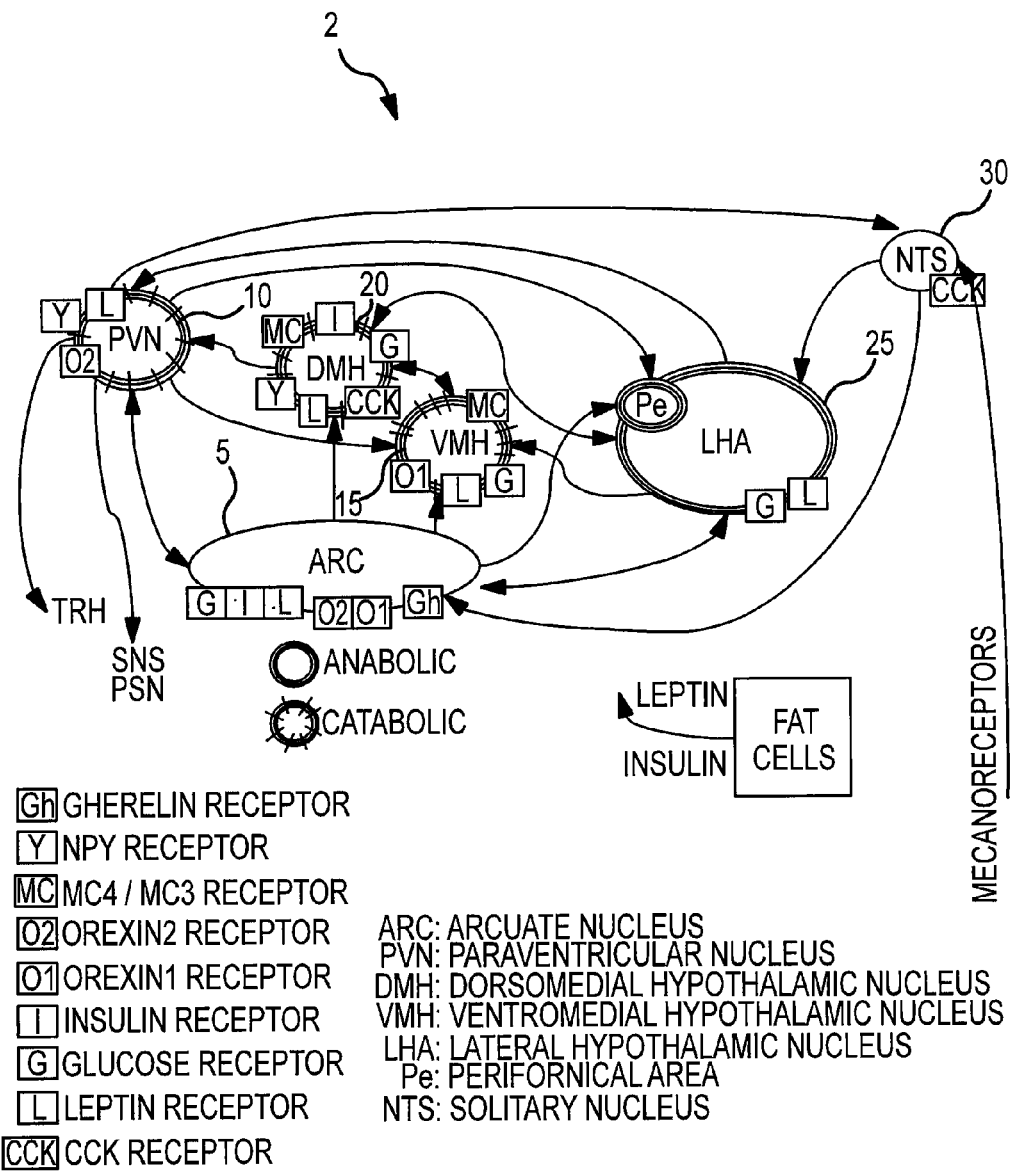

METHODS FOR IDENTIFYING AND TARGETING AUTONOMIC BRAIN REGIONS

This application claims the benefit of priority under 35 USC §119(e) to U.S. Patent Application No. 61/039,671, which was filed Mar. 26, 2008, and is entitled "Methods for Identifying and Targeting Autonomic Brain Regions," which is incorporated by reference herein in its entirety.

FIELD

The present disclosure relates generally to methods of identifying and targeting autonomic and autonomic-related brain regions using a targeting agent, such as an agonist and/or an antagonist of a receptor expressed by the targeted brain region and/or areas surrounding the targeted brain region.

BACKGROUND

One common technique to target brain regions, e.g., neural structures, that are part of the central nervous system (CNS) and are functionally connected with the autonomic nervous system (ANS) and that have no unique or clearly identified direct correlation with human senses (i.e., vision, hearing, touch, smell, and taste) is via anatomical references. These anatomical references are derived via population studies and the anatomical location in a particular patient may be identified using magnetic resonance imaging (MRI) and comparing the MRI anatomical image with the above-mentioned anatomical references derived via population studies.

In the only human case using deep-brain stimulation (DBS) targeting hypothalamic structures that are related to the energy homeostasis system and specifically the ventromedial hypothalamic nucleus (VMH), the target (i.e., the VMH) location was estimated using a computed tomographic scan (CT scan) which is similar to an MRI. The scan provided anatomical information to be used as a reference. After the electrode was at the estimated target, the electrode position was confirmed by asking the patient if he felt less hunger (i.e. subjective data).

Provided herein are methods of identifying and targeting autonomic and autonomic-related brain regions.

SUMMARY

In one embodiment, a method of identifying a brain region in a patient comprises administering to the patient an effective amount of a targeting agent that activates or inhibits a brain region and imaging the brain region, wherein the brain region is selected from the group consisting of the ventromedial hypothalamic nucleus, the perifornical region, the lateral hypothalamic area, the dorsomedial hypothalamic nucleus, the arcuate nucleus, and the paraventricular nucleus. In one embodiment, the brain region is the ventromedial hypothalamic nucleus. In another embodiment, the brain region is a sub-set of the ventromedial hypothalamic nucleus.

In another embodiment, the sub-set of the ventromedial hypothalamic nucleus is the dorsomedial portion. The target receptor of the target brain region may be selected from the group consisting of a delta-opioid receptor, a cannabinoid receptor 1 (CB1), a corticotropin-releasing factor receptor 2 (CRF-R2), a kappa-opioid receptor, a G-protein receptor 61 (GPR61), a G-protein receptor 26 (GPR26), a glucocorticoid-induced receptor (GIR), Leptin receptor. In another embodiment, the activity of the ventromedial hypothalamic nucleus is indirectly inhibited by administering a targeting agent such as glucose to the patient. In another embodiment, the receptor is the CB1 receptor and wherein the agonist is WIN 55212-2. In a further embodiment, the substance that indirectly modulates the ventromedial hypothalamic nucleus is glucose. In one embodiment, glucose is administered orally.

In other embodiments, the imaging step is performed using at least one functional imaging technique and/or at least one anatomical imaging technique. In one embodiment, the functional imaging is either functional magnetic resonance (fMRI) or positron emission tomography (PET). In another embodiment, the imaging is analyzed using Temporal Cluster Analysis (CTA). In one embodiment, the anatomical imaging is either magnetic resonance (MRI) or computer-tomography scan (CT scan).

In some embodiments, a method described herein comprises a last step of fine-tuning the identification of the brain region. For example, the step of fine-tuning may comprise monitoring at least one of oxygen consumption, energy expenditure, carbon dioxide production or respiratory quotient.

BRIEF DESCRIPTION OF THE DRAWINGS

FIG. 1 shows the relationship between hypothalamic nuclei and other brain regions.

DETAILED DESCRIPTION

Correctly identifying and targeting particular brain regions during neurosurgical procedures is useful for successful medical intervention. The present disclosure provides for methods of identifying of brain regions using targeting agents for brain regions, and imaging the brain region.

In certain embodiments, the disclosure provides methods of identifying deep brain regions that are the target in deep-brain stimulation (DBS). In some embodiments, the deep brain regions are hypothalamic regions with a known population of particular neurons which possess specific cellular receptors. Furthermore, the disclosure addresses the identification of hypothalamic regions involved in the energy homeostasis system. These regions may include sub-sets of the VMH, such as the dorsomedial portion of the VMH and the ventrolateral portion of the VMH, functional portions of the ventromedial hypothalamic nucleus (VMH), the perifornical region (Pe), the lateral hypothalamic area (LHA), the dorsomedial hypothalamic nucleus (DMH), the arcuate nucleus (ARC), and the paraventricular nucleus (PVN). These may be identified by a targeting agent. For example, they may be activated by one or more agonists and/or inhibited by one or more antagonists, many of which have a direct or indirect effect on energy expenditure, food consumption, glucose uptake in peripheral tissue, lipolysis, and other related functions of the energy homeostasis system, are identified and targeted.

An ordinarily skilled artisan will recognize that instead of using data obtained in a population study, the methods described herein may rely on data obtained before the surgery from each individual patient to fine-tune identification of the desired neural region(s) or structure(s), and confirm the placement of the electrode during the surgical procedure (intra-operatively) using both objective (e.g., EE, VCO2, VO2) and subjective (e.g., ask the patient to report on unpleasant sensations such as dizziness) measurements.

I. Identifying Brain Regions

The methods and apparatuses described herein identify brain regions by administering an effective amount of at least one first targeting agent that binds a target in a first brain region, and imaging the first brain region to create a first brain image. The target can be, for example, a receptor that are located on in the brain region. Since many brain regions contain the same receptors, one way to identify a particular brain region is by target receptors, or combination of receptors, located thereon. For example, a method as described herein can result in the direct or indirect stimulation or inhibition of the cells in the targeted brain region such that the brain region may be identified through at least one well-known functional imaging technique (e.g., fMRI, PET), and optionally, at least one well-known anatomical imaging technique (e.g., MRI, CT scan). Direct stimulation or inhibition can be done via at least one targeting agent, such as an agonist or antagonist, respectively. Indirect stimulation or inhibition can be achieved using a secondary substance such that the activity in the targeted brain region changes (i.e., stimulating or inhibiting the cells in the brain region); one of such examples would be ingesting glucose, which will, in a delayed manner, indirectly inhibit the activity in the VMH.

The term "targeting agent" refers to molecule or compound that binds a target in a target brain region. Suitable targets can include receptors at the brain region. Targeting agents include, but are not limited to, an agonist or an antagonist of a cellular receptor found in a particular brain region and/or a substance that may indirectly activate or inhibit a particular brain region. Targeting agents can target any target known in the art and can include any number of compounds known in the art (see, e.g., non-limiting examples provided in Tables 1-3 herein). In various embodiments, glucose may be a targeting agent.

An "effective amount" refers to the amount of a compound that, when administered to a subject, binds to a target in sufficient quantity to be detected by an imaging technique. The effective amount may vary depending, for example, on the compound, brain region, the age, weight, and/or health of the subject, and the judgment of the person administering the compound. An appropriate amount in any given instance may be ascertained by those skilled in the art or capable of determination by routine experimentation.

As described herein, in certain situations, the targeting agent specifically binds to a particular biological target, such as a particular receptor of a targeted brain region. The methods described herein are not limited to any particular targeting agent, and a variety of targeting agents can be used. The targeting agents can be, for example, various specific ligands, such as antibodies, monoclonal antibodies and their fragments, folate, mannose, galactose and other mono-, di-, and oligosaccharides, and RGD peptide.

Other examples of such targeting agents include, but are not limited to, nucleic acids (e.g., RNA and DNA), polypeptides (e.g., receptor ligands, signal peptides, avidin, Protein A, and antigen binding proteins), polysaccharides (e.g. glucose), biotin, hydrophobic groups, hydrophilic groups, drugs, and any organic molecules that bind to receptors. When two or more targeting agents are used, the targeting agents can be similar or dissimilar. Utilization of more than one targeting agent can allow the targeting of multiple biological targets or can increase the affinity for a particular target.

In some instances, the targeting agents are antigen binding proteins or antibodies or binding portions thereof. Antibodies can be generated to allow for the specific targeting of receptors of a particular brain region. Such antibodies include, but are not limited to, polyclonal antibodies; monoclonal antibodies or antigen binding fragments thereof, modified antibodies such as chimeric antibodies, reshaped antibodies, humanized antibodies, or fragments thereof (e.g., Fv, Fab', Fab, F(ab')2); or biosynthetic antibodies, e.g., single chain antibodies, single domain antibodies (DAB), Fvs, or single chain Fvs (scFv). Methods of making and using polyclonal and monoclonal antibodies are well known in the art, e.g., in Harlow et al, Using Antibodies: A Laboratory Manual: Portable Protocol I. Cold Spring Harbor Laboratory (Dec. 1, 1998). Methods for making modified antibodies and antibody fragments (e.g., chimeric antibodies, reshaped antibodies, humanized antibodies, or fragments thereof, e.g., Fab', Fab, F(ab')2 fragments); or biosynthetic antibodies (e.g., single chain antibodies, single domain antibodies (DABs), Fv, single chain Fv (scFv), and the like), are known in the art and can be found, e.g., in Zola, Monoclonal Antibodies: Preparation and Use of Monoclonal Antibodies and Engineered Antibody Derivatives, Springer Verlag (Dec. 15, 2000; 1st edition). In some instances, the targeting agents include a signal peptide. These peptides can be chemically synthesized or cloned, expressed and purified using known techniques. Signal peptides can be used to target brain regions as described herein.

In order to increase the signal-to-noise ratio when the target area or region is being stimulated, the activity in areas surrounding the target area may be inhibited. Conversely, in order to increase signal-to-noise ratio when the target area is being inhibited, the activity in areas surrounding the target area could be stimulated. Stimulation and inhibition of any area can be done by using the appropriate targeting agents.

Several imaging trials can be performed each one using at least one targeting agent, such as an agonist, such that the target region can be identified by identifying the region that is commonly activated in all trials so that by superimposing or fusing the results of all trials the target region may be identified. Each trial involves a different targeting agent that is common to the target region but not to the surrounding regions. The images may be superimposed or fused with respect to the other brain images. That is, in some embodiments, a first brain image may be superimposed on a second brain image. In other embodiments, a second brain image may be superimposed on a first brain image. Subsequent brain images may be superimposed or fused with the first and/or second brain images as needed. In some embodiments, the images are superimposed via manipulation with computer software. Examples of such software include ImageFusion (Integra Radionics, Burlington, Mass.) and iPlan RT Image (BrainLAB, Westchester, Ill.).

The particular targeting agent is selected according to the desired target and its surrounding areas. Table 1 lists potential receptor targets that may be available in a respective target brain region. Table 2 provides non-limiting examples of agonist and antagonist targeting agents that may be used for a particular target brain region and its surrounding areas. Table 3 provides non-limiting examples of combinations of agonist and antagonist targeting agents that may be used to identify a particular target region and its surrounding areas (i.e. "the objective"). It will be understood by those in the art that the target region can include structures

TABLE 1

Table with potential receptors

| Region | Potential (Human) Receptors |
|---|---|
| VMH (all) | Delta-opioid receptor (DOR) |
| | Cannabinoid receptor 1 (CB1) |
| | Corticotropin-releasing factor receptor 2 (CRF-R2) |
| | Kappa-opioid receptor (KOR) |
| | G-protein receptor 61 (GPR61) |
| | G-protein receptor 26 (GPR26) |

TABLE 1-continued

Table with potential receptors

| Region | Potential (Human) Receptors |
|---|---|
| | Glucocorticoid-induced receptor (GIR) |
| | Glucose (an agonist or antagonist of glucose is not needed, instead glucose is used a substance and it can be administered orally or intravenously.) |
| Dorsomedial portion of VMH | Orexin receptor 1 (OX1R) |
| | Orexin receptor 2 (OX2R) |
| | Melanocortin receptor 3 (MC3R) |
| | Neuropeptide Y receptor 5 (NPY-Y5R) |
| | Growth hormone-releasing hormone (GHRH) |
| | Melanin-concentrating hormone receptor 1 (MCHR1) |
| | Leptin |
| | Steroidogenic factor 1 (SF-1) |
| Ventrolateral portion of VMH | Melanocortin receptor 4 (MC4R) |
| Pe | KOR |
| | Mu-opioid receptor (MOR) |
| | MC4R |
| | MOR |
| | G-protein receptor 54 (GPR54) |
| LHA | Serotonin 2c (5-HT2c) |
| | MOR |
| | MCHR1 |
| DMH | KOR |
| | 5-HT2c |
| | MOR |
| | MCHR1 |
| | G-protein receptor 7 (GPR7) |

TABLE 1-continued

Table with potential receptors

| Region | Potential (Human) Receptors |
|---|---|
| | Prolactin releasing peptide receptor (PrRP-R) |
| | Glucagon-like peptide 1 receptor (GLP-1R) |
| | Corticotropin-releasing factor receptor 1 (CRF-R1) |
| | GPR26 |
| | GPR54 |
| | Leptin |
| ARC | KOR |
| | Neuropeptide Y receptor 1 (NPY-Y1R) |
| | NPY-Y5R |
| | GHRH |
| | MC3R |
| | GLP-1R |
| | CRF-R1 |
| | GPR61 |
| | GPR26 |
| | GIR |
| | GPR54 |
| | Leptin |
| PVN | KOR |
| | NPY-Y1R |
| | NPY-Y2R |
| | NPY-Y5R |
| | MCHR1 |
| | MC4R |
| | GLP-1R |
| | CRF-R2 |
| | GPR61 |

TABLE 2

Table with agonist and antagonist examples.

| Receptor (human) | Agonists | Antagonists |
|---|---|---|
| Delta-opioid receptor (DOR) | Deltorphin II | Naltrindole |
| Kappa-opioid receptor (KOR) | Butorphanol | Buprenorphine |
| Mu-opioid receptor (MOR) | codeine, PL017 | naloxone benzoylhydrazone |
| Cannabinoid receptor 1 (CB1) | WIN 55212-2 | SR141716A |
| Corticotropin-releasing factor receptor 1 (CRF-R1) | [$^{125}$I]-Tyr0-CRF, Sauvagine | α-helical CRF, Astressin |
| Corticotropin-releasing factor receptor 2 (CRF-R2) | Sauvagine | Astressin |
| Glucocorticoid-induced receptor (GIR) | BIIE0246 | |
| Growth hormone-releasing hormone (GHRH) | N(alpha)-5-carboxyfluoresceinyl-D-Ala(2), Ala(8), Ala(15), Lys(22) | N-Ac-Tyr1,D-Arg2 |
| Glucagon-like peptide 1 receptor (GLP-1R) | NN2211 | exendin (9-39) |
| Leptin receptor | Leptin | |
| Melanin-concentrating hormone receptor 1 (MCHR1) | Compand A (see: Lauren P. Shearman, et al) | T-226296 |
| Melanocortin receptor 3 (MC3R) | [D-Trp8]-g-MSH | PG9O1 |
| Melanocortin receptor 4 (MC4R) | RY764 | MCLO129 |
| Neuropeptide Y receptor 1 (NPY-Y1R) | [$^{125}$I]PYY, PYY | BIBP 3226, |
| Neuropeptide Y receptor 5 (NPY-Y5R) | [D-Trp$^{32}$]-NPY | L-152804 |
| Orexin receptor 1 (OX1R) | Orexin-A | SB-410220, [$^{3}$H]SB-674042 |
| Orexin receptor 2 (OX2R) | Orexin-B | 1-(2,4-dibromo-phenyl)-3-((4S,5S)-2,2-dimethyl-4-phenyl-[1,3]dioxan-5-yl)-urea |
| Prolactin releasing peptide receptor (PrRP-R) | PrRP-20 | |
| Serotonin (5-HT2c) | YM348, bromocriptine | LY334362, AC-90179 |
| G-protein receptor 54 (GPR54) | 4-fluorobenzoyl-Phe-Gly-Leu-Arg-Trp-NH2 | |

TABLE 3

Table listing examples of combinations of agonists and antagonists.

| Objective | First Ligand | Second Ligand |
|---|---|---|
| Activate the dmVMH and inhibit the rest of the VMH | Orexin-A | SR141716A |
| Activate the VMH except the dmVMH | WIN 55212-2 | SB-410220 |
| Activate the dmVMH and inhibit the vlVMH | [D-Trp8]-g-MSH | MCLO129 |
| Activate the Pe and inhibit the LHA and the DMH | 4-fluorobenzoyl-Phe-Gly-Leu-Arg-Trp-NH2 | LY334362 |

The structure of MCL0129 and RY764 are as follows:

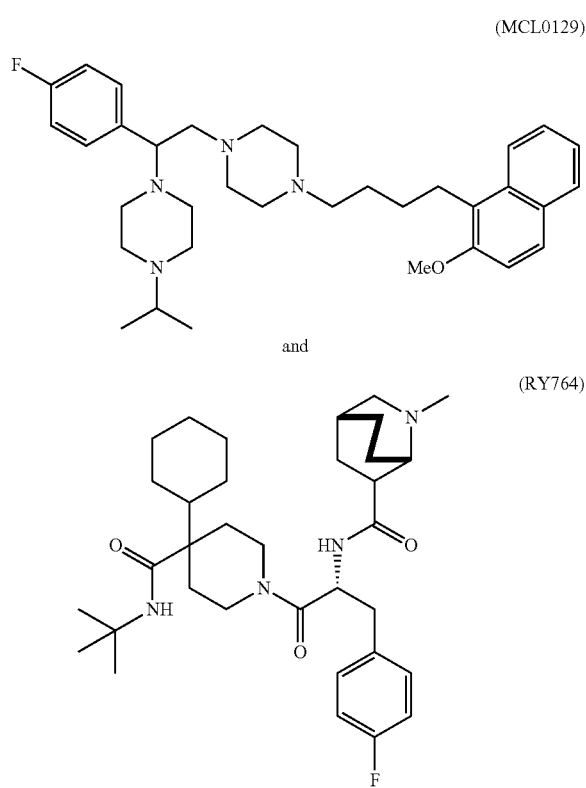

The sequence of PG901 is Ac-Nle-c[Asp-Pro-D-Nal(2')-Arg-Trp-Lys]-NH2 (PG901).

As can be understood with reference to Tables 1 and 2, for example, an ordinarily skilled artisan may use WIN 55212-2 (which is commercially available from vendors such as Perkin Elmer) as a CB1 agonist, [D-Trp8]-g-MSH as an MC3R agonist, RY764 as an MC4R agonist, PG9O1 as an MC3R antagonist, MCLO129 as an MC4R antagonist, etc. As another example, glucose can be ingested as a targeting agent. In some embodiments, glucose may be delivered by other methods known in the art, such as intravenously. Without being bound by mechanism, it may be likely that the action of glucose will be indirect, e.g., the activity in the VMH decreases when the glucose concentration in the blood is increased. Other agonists and antagonists of the receptors in Table 1 are well-known. For example, in one embodiment used to identify the dorsomedial portion of the VMH, Orexin-1 may be intravenously administered. Orexin-1 can cross the blood-brain barrier and thus may serve as an agonist to OX1R. Orexin 1 may also be called Orexin A or hipocretin-1.

After the targeting agent, e.g. the agonist(s) and/or antagonist(s) are selected, they may be administered to the patient. The administration can be done via many routes, for example, sub-cutaneous, intramuscular, intravenous, intracerebral ventricular, epidural, oral, or etc. The targeting agent may be given as either a bolus or a constant infusion. The dosage and/or rate mainly depends upon the particular targeting agent being used. In general, the given dosage and/or rate should not result in a toxic accumulation and will provide a perceptible activation of the target tissue.

Functional Magnetic Resonance Imaging (fMRI) and/or Positron Emission Tomography (PET) can be used to image and measure the activity of the desired brain region and of the entire brain. In some embodiments, temporal activity averaging technique such as Temporal Clustering Analysis (TCA) may also be used. TCA may be confirmed with ultrasound stimulation. Magnetic Resonance Imaging (MRI) and Computed Tomography Scan (CT scan) may also optionally be used to gather anatomical information. An ordinarily skilled artisan will recognize that when PET is used the agonists and antagonists should be altered so that they become radioactive isotopes.

An MRI antenna (also called MRI coil), such as the Dual Tune Head Coil, manufactured by MR Instruments of Minneapolis Minn. may also be used to increase the quality of the MRI image.

An activity map may be generated by combining images measuring the activity (e.g., several fMRI and/or several PET images) and anatomical images (e.g., MRI and/or CT-Scan). Given the introduction of targeting agents, desired target region may be more active than its surroundings and thus identified and localized. For example, utilizing an agonist targeting agent that activates the VMH along with utilizing an antagonist targeting agent or antagonist targeting agents that inhibit(s) the surrounding regions (e.g., the ARC and the DMH), generates a relatively higher activity signal arising from the VMH compared to utilizing the agonist alone.

In some embodiments, Temporal Clustering Analysis (TCA) may be used to interpret the data from the functional imaging techniques. For example, in traditional TCA, the images obtained from a fMRI brain scan are composed of a set of cubes representing volumetric data called voxels. In order to construct a time series of the images a set of voxels are obtained periodically. TCA may be used to identify groups of voxels that reach a peak in the fMRI signal at the same time, thus finding clusters of voxels for which their activity is correlated in time.

Another TCA method that may be used is a modified TCA as described by Yee et al, *Magnetic Resonance Imaging*, 20 (2002) 17-26. The modified TCA is based on the integrated signal intensity of a temporal cluster at each time point as opposed to a traditional TCA which is based only on the size of a temporal cluster at each time point) (See Yee et al. 17-26). A temporal cluster at each time point is defined, in both TCA methods, as a group of voxels reaching their maximum (or minimum) values at the same time. Compared with a traditional TCA, the modified TCA may have a higher sensitivity to detect activation peaks for determining time windows of brain responses.

After selecting a reference or the best available reference, the exact position of the target area is coded into 3D coordinates, which are then used to implant the electrode. The reference or best available reference can be chosen by using, for example, a stereotactic frame, a "frameless" stereotactic device, anatomical references or other appropriate reference. Stereotactic surgery works on the basis of three main components: 1) a stereotactic planning system, including atlas, multimodality image matching tools, coordinates calculator, etc, 2) a stereotactic device or apparatus and 3) a stereotactic localization and placement procedure. Stereotactic frame guidance and techniques, such as CT imaging, MRI targeting and microelectrode recording may be used to place chronic stimulating electrodes in the targeted area.

Modern stereotactic planning systems are computer based. The stereotactic atlas is a series of cross sections of anatomical structure (e.g. of the human brain), depicted in reference to a two-coordinate frame. Thus, each brain structure can be easily assigned a range of three coordinate numbers, which will be used for positioning the stereotactic device. In most atlases, the three dimensions are: latero-lateral (x), dorso-ventral (y) and rostro-caudal (z).

The stereotactic apparatus uses a set of three coordinates (x, y and z) in an orthogonal frame of reference (Cartesian coordinates), or, alternatively, a polar coordinates system, also with three coordinates: angle, depth and antero-posterior location. The mechanical device has head-holding clamps and bars which puts the head in a fixed position in reference to the coordinate system (the so-called zero or origin). In small laboratory animals, these are usually bone landmarks which are known to bear a constant spatial relation to soft tissue. For example, brain atlases often use the external auditory meatus, the inferior orbital ridges, the median point of the maxilla between the incisive teeth. or the bregma (confluence of sutures of frontal and parietal bones), as such landmarks. In humans, the reference points, as described above, are intracerebral structures which are clearly discernible in a radiograph or tomogram.

Guide bars in the x, y and z directions (or alternatively, in the polar coordinate holder), fitted with high precision vernier scales allow the neurosurgeon to position the point of a probe (an electrode, a cannula, etc.) inside the brain, at the calculated coordinates for the desired structure, through a small trephined hole in the skull.

Currently, a number of manufacturers produce stereotactic devices fitted for neurosurgery in humans, as well as for animal experimentation. Examples of such stereotactic devices include, Leksell Stereotactic Frame (Elekta, Atlanta, Ga.), CRW Stereotactic Frame (Integra Radionics, Burlington, Mass.) (for human use), large and small animal Stoelting stereotactic frame (Stoelting Co., Wood Dale, Ill.), large and small animal Stereotactic Instruments (Harvard Apparatus, Holliston, Mass.) Example of a "frameless" stereotactic device or a device used in a "frameless" surgery include VectorVision, made by BrainLAB of Westchester, Ill.

In some embodiments the modulation of the activity of the identified and targeted brain region is performed via implanted electrodes. In other embodiments, the modulation of the activity of the brain region is performed via local drug delivery. In other embodiments, the modulation of the activity is performed by a combination of implanted electrodes and local drug delivery. In yet other embodiments the modulation of the activity of the brain region is performed via non-invasive methods such as ultrasound, transcranial magnetic stimulation (TMS), and/or energy beams that can change the temperature in the target tissue. Additionally, beam directed energy, either ionizing (DeSalles et al., *Acta Neurochir Suppl.*, 2008) or non-ionizing radiation (Tyler et al., PLOS One, 2008), may be used to modulate the brain circuitry.

When certain portions of the brain region are stimulated an immediate increase in energy expenditure (EE) and lipolysis is expected, e.g. when stimulating the dorsomedial portion of the VMH specifically. Therefore, in order to fine tune the location and/or identification of the brain region, e.g., verify that the modulation is being applied to the desired targeted brain region, at least one of the following is monitored: a) the oxygen consumption (VO2), b) the energy expenditure (EE), c) the carbon dioxide production (VCO2), and d) the respiratory quotient (RQ=VCO2/VO2). As used herein, "fine-tune" means verifying the location and/or identification, and/or refine the identification of, the target region.

In some experiments, as can be understood from the Examples found below, EE, VO2, VCO2, and RQ may be monitored using indirect calorimetry. Indirect calorimetry uses the overall oxygen consumption and the carbon dioxide production of a subject to estimate the rate at which the patient is expending energy, that is, indirect calorimetry is used to estimate the overall metabolic rate of the patient. The oxidation of each macro-nutrient (i.e. fats, carbohydrates and proteins) requires a specific amount of oxygen ($O_2$) and produces a specific amount of carbon-dioxide ($CO_2$), water ($H_2O$), and energy. The energy produced can be computed from the specific chemical reaction depending on the particular nutrient.

Using indirect calorimetry, an increase in lipolysis is signaled by a decrease in the RQ. When the target area is one that controls the overall metabolic rate and/or the percentage of oxidation of the main nutrients (i.e., carbohydrates, proteins, and fats), for example the VMH, indirect calorimetry may be used during the implantation procedure to fine tune the identification of the target. In this case, as the electrode approaches the coordinates of the target area, a small current is passed into the tissue through at least one electrode pole while indirect calorimetry is performed. Since indirect calorimetry measures the energy expenditure (i.e., the metabolic rate) as well as the respiratory quotient (RQ), the indirect calorimetry measurements will reveal when the target is reached. After the target region is reached, the electrode is fixed in place using standard neurosurgical techniques. The RQ changes when the oxidation-rate ratio carbohydrates/fats changes. The energy expenditure increases and RQ decreases when the dorsomedial portion of the VMH is stimulated with low-intensity currents. The energy expenditure may increase if a larger current is used. In animal models, the RQ may increase (sometimes only transiently) as the current is increased. Protocols for implementation or performance of indirect calorimetry are known.

II. Deep Brain Stimulation

Deep brain stimulation (DBS) is a surgical treatment involving the implantation of a medical device which sends electrical impulses to specific parts of the brain. In some embodiments, the device is referred to as a brain pacemaker. DBS directly modulates brain activity in a controlled manner. In various embodiments, its effects are reversible (unlike those of lesioning techniques).

Generally, the deep brain stimulation system includes three components: an implanted pulse generator (IPG), a lead, and an extension. The IPG is a pulse generator use to stimulate excitable tissue such as nerve tissue. The IPG can by battery-powered or inductibly-powered or powered by a combination of a battery and inductibly-transmitted energy. IPGs are often encased in a biocompatible hermetic housing, such as a titanium case.

When an IPG is used to stimulate brain tissue, electrical pulses are delivered to the brain to modulate neural activity at the target site. The IPG may be calibrated by a neurologist, nurse or trained technician to optimize symptom suppression and control side effects. At its proximal end, the lead is electrically connected to the IPG either directly or via the extension. At its distal end, the lead is in contact with the target tissue via at least one electrode or contact point. In some embodiments, the lead may be a coiled wire insulated in polyurethane with four platinum iridium electrodes and is placed in the target area of the brain.

Various commercial IPG may be used in various embodiments of the present disclosure. For example, commercial embodiment known in the art can be used. In certain embodiments, IPG that can be used include the Medtronic Soletra or Kinetra IPGs (Medtronic, Minnesota), Libra (St. Jude, Minnesota), used conventionally for DBS. Alternatively, a DBS developed to treat pain, such as the Restore and Restore Ultra IPGs (Medtronic, Minnesota), Eon, Eon mini, Renew, or Genesis (St. Jude, Minnesota), or Precision Plus (Boston Scientific Natick, Mass.). The IPG can be used for additional indications, including epilepsy (Responsive Neurostimulator system, Neuropace, Mountain View, Calif.), vagal neural signals (Maestro, Enteromedics St. Paul, Minn.), cochlear implants (Freedom, Cochlear Limited, Lane Cove, Australia), as well as other uses (Interstim II and Enterra, Medtronic, Minneapolis).

Examples of such DBS devices include, but are not limited to, devices designed for control of Parkinson's Syndrome, such as the Kinetra Model 7428 Neurostimulator or the Soletra Model 7426 Neurostimulators (Medtronic, Minnesota). The power source(s) generate electrical signals that are transmitted to the brain via extensions. Examples of such extensions include, for example, Model 7482 Extensions or two Model 7495 Extensions (Soletra), or either two Model 3387 DBS Leads or two Model 3389 DBS Leads. Other devices can be used for tremor control therapy. Examples of these devices include power sources therapy can include one single program Soletra Model 7426 Neurostimulator or one single program Model 7424 Itrel II Neurostimulator. The power source generates electrical signals that are transmitted to the brain via either one Model 7495 Extension or one Model 7482 Extension and either one Model 3387 DBS Lead or one Model 3389 DBS Lead. These components comprise the implantable portion of the Activa System for unilateral Activa Tremor Control Therapy (Medtronic, Minnesota).

In various embodiments, an electrode may be inserted at the brain region to allow the brain region to be identified at a later time for therapeutic treatment. For example, a lead that contains an electrode is implanted after targeting a specific brain region. The electrode remains at least until such a time as DBS is applied.

In various embodiments, the IPG is configured to deliver DBS at a one or more frequencies, or within a range of frequencies. The IPG can be configured to deliver electrical stimulation at frequencies less than, and/or greater than one or more of 50 Hz, 45 Hz, 40 Hz, 35 Hz, 30 Hz, 25 Hz, 20 Hz, 15 Hz, or 10 Hz. In various embodiments, the IPG can be configured to deliver electrical stimulation at frequencies greater than, and/or less than, one or more of 50 Hz, 60 Hz, 70 Hz, 80 Hz, 90 Hz, 100 Hz, 125 Hz, 150 Hz, 175 Hz, 200 Hz, 225 Hz, 250 Hz, 275 Hz, 300 Hz, 325 Hz, 350 Hz, 375 Hz, 400 Hz, 425 Hz, 450 Hz, 475 Hz, or 500 Hz. In various embodiments, the IPG can be configured to deliver electrical stimulation at a frequency greater than, and or less than, one of 500 Hz, 525 Hz, 550 Hz, 575 Hz, 600 Hz, 625 Hz, 650 Hz, 675 Hz, 700 Hz, 725 Hz, 750 Hz, 775 Hz, 800 Hz, 825 Hz, 850 Hz, 875 Hz, 900 Hz, 925 Hz, 950 Hz, or 975 Hz, or 1000 Hz. In various embodiments, the IPG can be configured to deliver electrical stimulation at greater and/or less than one or more of 1000 Hz, 2000 Hz, 3000 Hz, 4000 Hz, 5000 Hz, 6000 Hz, 7000 Hz, 8000 Hz, 9000 Hz, or 10000 Hz. In various embodiments, any of the above-referenced frequencies can be the upper or lower borders of an applied frequency.

The frequencies can be used for various embodiments. For example, depending on the particular neural system, lower frequencies tend to excite the neural elements (i.e. neural tissues), such neurons, axons, dendrites, nerve endings, nerve bundles, while higher frequencies tend to preferentially excite axons and in some cases inhibit neurons, and even higher frequencies tend to inhibit all neural elements. By way of example but not limitation, low frequency electrical stimulation may be used to produce a net excitatory effect, or alternatively to produce a net inhibitory effect.

In various embodiments, the IPG is configured to deliver DBS via different waveforms. For example, square monophasic, square biphasic with or without charge balanced, sinusoidal, ramp, triangular, exponential, and/or any combination of theses waveforms.

In various embodiments, the IPG is configured to deliver DBS at a specific pulse width or range of pulse widths. The IPG can be configured to deliver pulse widths in the range greater than and/or less than one or more of 10 μs, 20 μs, 30 μs, 40 μs, 50 μs, 60 μs, 70 μs, 80 μs, 90 μs, 100 μs, 125 μs, 150 μs, 175 μs, 200 μs, 225 μs, 250 μs, 275 μs, 300 μs, 325 μs, 350 μs, 375 μs, 400 μs, 425 μs, 450 μs, 475 μs, 500 μs, 525 μs, 550 μs, 575 μs, 600 μs, 625 μs, 650 μs, 675 μs, 700 μs, 725 μs, 850 μs, 875 μs, 900 μs, 925 μs, 950 μs, 975 μs, 1000 μs, 1500 μs, 2000 μs, 2500 μs, or 3000 μs. Those of skill in the art will recognized that one or more of the above times can be used as border of a range of pulse lengths. Pulse lengths can be defined in terms of extremely short pulses (i.e. between 10 and 50 μs), short pulses (i.e. between 50 to 350 μs), medium width pulses (i.e. between 350 to 700 μs), long pulses (i.e. between 700 us to 1.5 ms), very long pulses (i.e. between 1.5 to 3 ms), and extremely long pulses (i.e. >3 ms). Without being limited to any mechanism or mode of action, in certain cases longer pulses can excite fast and slower conducting neural elements such as smaller diameter axons as well as neurons for a given amplitude, while shorter pulses can excite fast conducting neural elements such as big diameter axons.

In various embodiments, the IPG is configured to deliver DBS electrical stimulation at a range of voltage or current amplitudes, which in various embodiments can be voltage controlled, current controlled, or a combination of both (i.e., the IPG produces current controlled pulses as well as voltage controlled pulses). In other embodiments, the amplitude can be applied by a capacitive discharge. In various embodiments, the amplitude can be in a range greater than and/or less than one or more of 5 μA, 6 μA, 7 μA, 8 μA, 9 μA, 10 μs, 20 μA, 30 μA, 40 μs, 50 μA, 60 μA, 70 μA, 80 μA, 90 μA, 100 μA, 125 μA, 150 μA, 175 μA, 200 μA, 225 μA, 250 μs, 275 μA, 300 μA, 325 μA, 350 μA, 375 μA, 400 μA, 425 μA, 450 μA, 475 μA, 500 μA, 525 μA, 550 μA 575 μA, 600 μA, 625 μA, 650 μA, 675 μA, 700 μA, 725 μA, 850 μA, 875 μA, 900 μA, 925 μA 950 μA, 975 μA, 1 mA, 2 mA, 3 mA, 4 mA, 5 mA, 6 mA, 7 mA, 8 mA, 9 mA, 10 mA, 20 mA, 30 mA, 40 mA or 50 mA. Those of skill in the art will recognized that one or more of the above amplitudes can be used as border of a range of amplitudes. Further, amplitudes can be described in terms of extremely low amplitudes (i.e. <10 uA and its equivalent voltage depending on the electrode(s)-tissue impedance), very low amplitudes (i.e. 10 to 100 uA and its equivalent voltage depending on the electrode(s)-tissue impedance), low amplitudes (i.e. 100 to 500 uA and its equivalent voltage depending on the electrode(s)-tissue impedance), medium amplitudes (i.e. 500 uA to 1 mA and its equivalent voltage depending on the electrode(s)-tissue impedance), high amplitudes (i.e. 1 mA to 5 mA and its equivalent voltage depending on the electrode(s)-tissue impedance), very high amplitudes (i.e. 5 mA to 10 mA and its equivalent voltage depending on the electrode(s)-tissue impedance), and extremely high amplitudes (i.e. >10 mA and its equivalent voltage depending on the electrode(s)-tissue impedance).

The actual amplitude can depend on several factors such as the distance between the electrode(s) and the target tissue, the distribution of the target tissue, the geometry of the electrode(s), the relative geometry and position between opposite and same polarity electrodes, the waveform, the actual polarity of the leading pulse, and other stimulation parameters such as frequency and pulse width. In order to reach a particular stimulation threshold (for a single neural element or for a given percentage of a population of neural elements such that a response is triggered), the amplitude, pulse width and frequency are not independent. In most cases the relationship between the amplitude, pulse width and frequency can be described by what is know in the art as strength-duration (S-D), strength-frequency (S-F), and strength-duration-frequency (S-D-F) curves, which can follow an exponential or hyperbolic mathematical form. The S-D-F curve is a 3 dimensional version of the better known 2 dimensional cases S-D and S—F curves.

In various embodiments, at least one of the IPG and lead of the DBS system are surgically implanted inside the body. In some embodiments at least one burr hole, which size can be any size known in the art which allows the placement and fixation of the at least one lead positioning and anchoring the lead correctly. The electrode is inserted, with instrumental feedback and/or feedback from the patient for optimal placement. In certain embodiments, the lead is connected to the IPG by the extension. In one embodiment, the extension is an insulated wire that runs from the head and down the side of the neck behind the ear to the IPG. In some embodiments it may be placed subcutaneously below the clavicle. In some embodiments, it may be placed subcutaneously behind the abdomen, in yet other embodiments where the IPG is cranially mounted the extension may be placed subcutaneously in the head.

DBS leads are placed in the brain according to the type of symptoms to be addressed. For example, in non-Parkinsonian essential tremor, the lead is placed in the ventrointermedial nucleus (VIM) of the thalamus. For the treatment of dystonia and symptoms associated with Parkinson's disease (rigidity, bradykinesia/akinesia and tremor), the lead may be placed in either the globus pallidus or subthalamic nucleus. Methods of identifying these regions are also described in more detail below.

III. Overview of the Energy Homeostasis System

The energy-homeostasis system includes both hypothalamic and extra-hypothalamic centers that are involved in processes regulating both the energy intake ($E_{IN}$) and the total energy expenditure (TEE). While $E_{IN}$ has one component, food intake ($F_{IN}$), the TEE can be divided into two main components: the energy expended due to movement-related activities and the energy expended due to non-movement-related activities. This division is such that at any given time the sum of these two components is equal to the TEE. In various aspects, the movement-related energy expenditure can be the mechanical energy expenditure (MEE) and the non-mechanical energy expenditure (nMEE) as the difference between the TEE and the MEE (Harnack et al., *Journal of Neuroscience Methods*). In humans the nMEE represents up to 70% of the TEE (McClean et al, *Animal and Human Calorimetry*). The fact that body weight (BW) remains relatively constant is due to the proper regulation of the nMEE.

Several mutually interacting hypothalamic nuclei may influence the MEE by inducing a change in spontaneous locomotor activity (Castenada et al, *Journal of Nutrition*) and shivering thermogenesis (Thornhill et al., *Canadian Journal of Physiology and Pharmacology*). These same mutually interacting hypothalamic nuclei may also regulate both the $F_{IN}$ and the nMEE through a net of complexly-interacting nuclei described below.

As can be understood from FIG. 1, at least five hypothalamic nuclei: Arcuate Nucleus (ARC) 5, Paraventricular (PVN) 10, Ventromedial Hypothalamic Nucleus (VMH) 15, Dorsomedial Hypothalamic Nucleus (DMH) 20 and the Lateral Hypothalamic Area (LHA) 25, may be involved in the regulation of the $F_{IN}$ and the nMEE. Some of the afferent and efferent connections to and from these nuclei and their molecular mechanisms are known. In addition, at least part of the nMEE regulation may be exerted via sympathetic and parasympathetic modulation (Berthoud, *Neuroscience and Biobehavioral Reviews*). Indirect connections between hypothalamic nuclei and the vagus nerve via the nucleus of the solitary tract (NTS) may also provide signals that influence the $F_{IN}$.

a. The Arcuate Nucleus (ARC)

As shown in FIG. 1, the ARC 5, located at the inferior medial tuberal hypothalamic region, receives information from circulating molecules due to a leaky blood-brain-barrier in the area (at the median eminence) (Broadwell et al., *Journal of Comparative Neurology*), and from direct neuronal inputs. The ARC 5 may act as both an integrative center and a command center for the energy homeostasis system 2. In particular, signaling-molecules circulating in the blood are monitored to detect whether long-term energy (e.g. leptin), middle-term energy (e.g. insulin) and/or short-term energy (e.g. glucose and ghrelin) is available (Berthoud, *Neuroscience and Biobehavioral Reviews*; Bagnol, *Current Opinion in Drug Discovery and Development*). Generally, leptin, which is produced by adipose tissue, circulates in the blood stream in a concentration that is proportional to the amount of total body-fat tissue. Under abnormal circumstances, leptin concentration in the blood may be transiently uncorrelated to the total body-fat content (Kennedy et al., *Journal of Clinical Endocrinology and Metabolism*). The concentration of ghrelin, a hormone produced in the epithelial cells in the stomach (Wynne, *Journal of Endocrinology*), is at its lowest point after a meal, and the concentration level may increase until the next meal (Cowley, *Neuron*). The ARC 5 receives neuronal inputs from regions inside and outside the hypothalamus. Its intra-hypothalamic afferents originate mainly at the PVN 10, the LHA 25 and the VMH 15. Most of its extra-hypothalamic afferents originate at the NTS 30 (also known as the solitary nucleus), the amygdala, and the bed nucleus of the striaterminalis (Berthoud, *Neuroscience and Biobehavioral Reviews*; DeFalco et al., *Science*).

The ARC 5 may include at least two different neuronal populations that produce functionally antagonistic signaling molecules. One population produces pro-energy-conserving signaling molecules (ECm) and the other population produces pro-energy-expending signaling molecules (EEm). To regulate both $F_{IN}$ and nMEE, these signaling molecules influence neuronal activity in other hypothalamic nuclei and in the ARC 5 (Williams et al., *Physiology & Behavior*). The pro-energy-conserving population produces neuropeptide-Y (NPY) and agouti gene-related peptide (AgRP), both of which possess potent energy-conserving effects (Hahn et al., *Nature Neuroscience*; Broberger, *Proceedings of the National Academy of Sciences of the United States of America*). The pro-energy-expending population produces pro-opiomelanocortin (POMC) and cocaine-and-amphetamine regulated transcript (CART) (Elias et al., *Neuron*; Kristensen, *Nature*). The POMC is a precursor to the α-melanocyte-stimulating hormone (α-MSH), and both the (α-MSH and CART reduce FIN and increase nMEE. The production of NPY/AgRP may be inhibited by NPY (NPY-Y2 receptor) (Broberger et al., *Neuroendocrinology*), α-MSH (ARC MC3 receptor) (Jobst et al., *Trends in Endocrinology and Metabolism*), leptin (Baskin et al., *Journal of Histochemistry & Cytochemistry*; Mercer et al., *Journal of Neuroendocrinology*), and insulin (Wang et al., *Brain Research*). The production of NPY/AgRP may be promoted by orexin (ORX) which is produced in the LHA 25 (Guan et al., *Neuroreport*; Horvath et al., *Journal of Neuroscience*; Peyron et al., *Journal of Neuroscience*), by ghrelin (Wynne, *Journal of Endocrinology*), and by circulating glucocorticoids (Williams et al., *Physiology & Behavior*). The production of POMC/CART may be decreased by α-MSH (ARC MC3 receptor) (Jobst et al., *Trends in Endocrinology and Metabolism*) and increased by leptin (Jobst et al., *Trends in Endocrinology and Metabolism*). However, medial VMH neurons, which may be directly or indirectly stimulated by POMC, send excitatory projections to POMC neurons in the ARC 5 (Sternson et al., *Nature Neuroscience*) thereby driving the melanocortin system.

The efferent pathways of these populations project mainly into other hypothalamic nuclei but also to extra-hypothalamic regions (Broberger et al., *Proceedings of the National Academy of Sciences of the United States of America*; Broberger et al., *Physiology & Behavior*). Efferent connections of the NPY/AgRP population project to the PVN 10, LHA 25, DMH 20, and VMH 15 (Berthoud et al., *Neuroscience and Biobehavioral Reviews*; Wynne et al., *Journal of Endocrinology*; Williams et al., *Physiology & Behavior*). Efferent connections to the POMC/CART population projects to the LHA 25 (e.g. into ORX producing neurons) (Elias et al., *Neuron*) and DMH 20 (e.g. NPY producing neurons). The POMC/CART-ARC neurons have direct projections to the VMH 15 (Wynne et al., *Journal of Endocrinology*; Guan et al., *Molecular Brain Research*) and the latter has numerous melanocortin receptors to which POMC binds (e.g. MC4r and MC3r) (Berthoud et al., *Neuroscience and Biobehavioral Reviews*; Bagnol et al., *Current Opinion in Drug Discovery & Development*; Wynne et al., *Journal of Endocrinology*).

In summary, the neuronal activity in the ARC 5 tends to balance the TEE and the FIN. The ARC 5 monitors the energy status in the body and may act upon other hypothalamic nuclei in order to compensate for an imbalance in the energy system.

b. Paraventricular Nucleus (PVN)

The PVN 10 is located in the superior periventricular chiasmatic hypothalamic region. The PVN 10 is involved in several regulatory systems including the energy-homeostasis system. A decrease in the $F_{IN}$ and an increase in nMEE, caused by the electrical stimulation of the PVN 10, appears to be mediated by the potentiation of GABA-ergic interneurons. Afferent projections from the ARC 5 and from the DMH 20 that release NPY/AgRP and NPY respectively, inhibit GABA-releasing interneurons. The POMC/CART projections increase GABA release from the same interneurons into the PVN 10 (Cowley et al., *Neuron*). Other afferent projections into the PVN 10 originate at ORX-producing neurons in the LHA 25. These LHA-neurons may mediate their effect through the orexin receptor-2 (OX2r), which is abundant in the PVN 10 (Bagnol et al., *Current Opinion in Drug discovery & Development*). OX2r may modulate arousal in sleep-wakefulness cycles (Lin et al., *Cell*) but may not modulate $F_{IN}$ because $F_{IN}$ is affected by OXR acting upon OX1r (Lecea et al., *Proceedings of the National Academy of Sciences of the United States of America*; Haynes et al., *Peptides*). Non-endocrine efferents from the PVN 10 project to several hypothalamic nuclei, including the ARC 5, VMH 15, DMH 20, and LHA 25 (Terhorst et al., *Brain Research Bulletin*). Extrahypothalamic efferent projections from the PVN 10 terminate in the NTS 30 and in the preganglionic neurons. The projections that terminate in the NTS 30 trigger neuronal activity that exert an inhibitory effect in the dorsal motor nucleus (Zhang et al., *American Journal of Physiology-Gastrointestinal and Liver Physiology*). In turn, the dorsal motor nucleus has an excitatory effect on the autonomic nervous system (ANS) (Nishimura et al., *Journal of Neurophysiology*).

In summary, the PVN 10 receives inputs from and sends outputs to most hypothalamic nuclei involved in the energy-homeostasis system 2. The PVN 10 also projects to both sympathetic and parasympathetic neurons and thereby functioning as an integrating, processing, and actuating center for the energy-homeostasis system 2.

c. Ventromedial Hypothalamic Nucleus (VMH)

The VMH 15 is located in the medial tuberal hypothalamic region. The VMH 15 has been implicated in metabolic (Ruffin et al., *Brain Research*), reproductive (Nishimura et al., *Journal of Neurophysiology*), affective (Kruk, *Neuroscience and Biobehavioral Reviews*), and locomotor (Narita et al., *Behav. Brain Res.*) behavior. The VMH 15 may be anatomically divided into four regions that may be only slightly connected or completely unconnected. These four regions are the anterior VMH (aVMH), ventrolateral VMH (vlVMH), central VMH (cVMH), and dorsomedial VMH (dmVMH) (Canteras et al., *Journal of Comparative Neurology*).

Within the energy-homeostasis system, the VMH 15 has been referred to as the "satiety center" (Schwartz et al., *Nature*). In addition, stimulation of the VMH may increase locomotor activity (Narita et al., *Behav. Brain Res.*), non-mechanical energy expenditure (nMEE), decrease $F_{IN}$ (Ruffin et al., *Brain Research*), promote lipolysis (Ruffin et al., *Brain Research*; Takahashi et al. *J of the Autonomic Nervous System*; Shimazu, *Diabetologia*), and stimulate non-shivering thermogenesis (Thornhill et al., *Brain Research*). Experiments have also shown that VMH activity may regulate glucose uptake in skeletal muscles during exercise (Vissing et al., *American Journal of Physiology*) and that lesions in the VMH 15 may produce obesity and hyperphagia (Williams et al., *Physiology & Behavior*). The activity in the VMH may be influenced by both short and long-term energy availability because it contains numerous leptin receptors (Shioda et al., *Neuroscience Letters*) and close to half of its neurons are stimulated by a glucose increase (Ashford et al., *Pflugers Archiv-European Journal of Physiology*; DunnMeynell et al., *Brain Research*; Muroya et al., *Neuroscience Letters*). In particular, the activity of the gluco-sensitive neurons in the VMH 15 is up-regulated by leptin and down-regulated by ORX (originating in the LHA) (Shiraishi et al., *Physiology & Behavior*).

The VMH 15 receives afferent projections from the ARC 5 (e.g. NPY/AgRP and POMC/CART neurons) (Wynne et al., *Journal of Endocrinology*), the LHA 25 (e.g. ORX and melanin-concentrating hormone neurons) (Jobst et al., *Trends in Endocrinology and Metabolism*), the DMH 20, the PVN 10, the ANH (Terhorst et al., *Brain Research Bulletin*), and the NTS 30 (Fulwiler et al., *Neuroscience Letters*). In addition to projecting efferent fibers to all of the above nuclei, the VMH 15 also projects to the PHA, the zona incerta (ZI), limbic areas, several thalamic nuclei, the amygdala, the periaqueductal gray, and to the entorhinal area (Canteras, et al., *Journal of Comparative Neurology). Medial VMH neurons, which may be influenced by POMC produced by ARC neurons, send excitatory projections to POMC neurons in the ARC (Sternson et al., *Nature Neuroscience*) which may help to drive the melanocortin system.

In summary, the VMH 15 is anatomically divided and these divisions may be functionally different. With respect to the energy-homeostasis system, the VMH 15 integrates information about short-term and long-term energy availability and it may have functional connections with most of the other hypothalamic nuclei involved in the energy-homeostasis system. Thus, VMH activity may influence $F_{IN}$, MEE, nMEE, lipolysis, and glucose uptake in muscles.

d. Dorsomedial Hypothalamic Nucleus (DMH)

The DMH 20 is located in the medial tuberal region just dorsal to the VMH 15. Lesions in the DMH may cause changes in pancreatic-nerve activity (Elmquist et al., *Proceedings of the National Academy of Sciences of the United States of America*) and may induce hypophagia, thereby leading to a lower body weight (BW) (Bernardis et al., *Proceedings of the Society for Experimental Biology and Medicine*) and stimulation of the DMH may result in hyperglycemia (Elmquist et. al., *Proceedings of the National Academy of Sciences of the United States of America*). These effects may be carried out via NPY-expressing neurons in the DMH that project to the PVN (Berthoud, *Neuroscience and Biobehavioral Reviews*).

From within the hypothalamus, the DMH 20 receives afferent projections from the VMH 15, the LHA 25, the ARC 5, and the anterior hypothalamic nucleus (AHN). From outside the hypothalamus, the DMH 20 may receive afferent projections from the periaqueductal gray, the hippocampal formation (e.g. ventral subiculum) and from the prefrontal cortex (Thompson et al., *Brain Research Reviews*). In addition, the DMH 20 may receive inputs for leptin and insulin receptors as well as from gluco-sensitive neurons expressed in the nucleus. The DMH 20 projects mainly to other hypothalamic nuclei, in particular to the PVN 10 but may also project to the VMH 15 and to the AHN, among others.

In summary, the DMH 20 may constitute an integrative center for intra- and extra-hypothalamic inputs that modulate aspects of the energy-homeostasis system, and such modulation may occur by influencing PVN 10 activity.

e. Lateral Hypothalamic Area (LHA)

The LHA 25 has extensive connections both inside and outside the hypothalamus. It sends and receives projections to and from the cortex, the thalamus, the basal ganglia, the mid-brain, the hippocampal formation, the NTS 30, and most hypothalamic regions (Berthoud, *Neuroscience and Biobehavioral Reviews*; Wynne et al., *Journal of Endocrinology*; Williams et al., *Physiology & Behavior*; Jobst et al., *Trends in Endocrinology and Metabolism*). In particular, information from the GI tract reaches the LHA 25 via the NTS 30 (Woods, *AJP-Gastrointestinal and Liver Physiology*).

The LHA may also receive information from circulation through leptin receptors (Elmquist, *Neuroendocrinology of Leptin*) and numerous gluco-sensing neurons that increase their firing rate in response to a decrease in circulating glucose (Ashford et al., *Pflugers Archiv-European Journal of Physiology*). In particular, a decrease in glucose may cause an increase in ORX production in the LHA 25 (Hakansson et al., *Journal of Neuroendocrinology*; Chemelli et al. *Cell*), which in turn may stimulate $F_{IN}$ acutely (Bayer et al., *Neuroreport*). There are two types of ORX molecules produced in the LHA 25, Orexin-A (ORXa) and Orexin-B (ORXb) (Peyron et al., *Journal of Neuroscience*; Sakurai et al., *Cell*) and two receptors have been found to which ORX binds: OX1R and OX2R.

The OX1R may have a much higher affinity (approximately 10-fold) for ORXa than for ORXb, while the other ORX receptor, OX2R, may have similar affinities for both ORXa and ORXb (Lund et al., *Journal of Biological Chemistry*). Experimental data suggests that only ORXa is directly related to the energy-homeostasis system. Intraventricular injections of ORXa may acutely promote feeding (de Lecea et al., *Proceedings of the National Academy of Sciences of the United States of America*; Haynes et al., *Peptides*), and blocking its effects with a specific antagonist may reduce $F_{IN}$ (Yamada et al., *Biochemical and Biophysical Research Communications*). ORXb may play an important role in the arousal part of the sleep-wakefulness cycle, as shown by OX2R knockout-mice experiments in which the animals develop narcolepsy (Chemelli et al. *Cell*). In contrast to the VMH, where OX1R is heavily expressed, the PVN contains a substantial amount of OX2R (Bagnol, *Current Opinion in Drug Discovery & Development*). In the VMH 15, ORXa may inhibit the activity of gluco-sensitive neurons thus attenuating the response of the VMH 15 to an increase in the circulating glucose (Shiraishi et al., *Physiology & Behavior*). Experimental data suggests that both OX1R and OX2R are expressed in the ARC where they modulate, for example, NPY/AgRP and POMC/CART neurons (Burdakov et al., *Journal of Neuroscience*; Suzuki et al., *Neuroscience Letters*).

In summary, the LHA 25 receives information from many systems including the GI tract. The LHA 25 integrates information from all of these systems, and in turn, influences the expression of ECm and EEm in the ARC 5 as well as the glucose sensitivity in the VMH 15.

IV. Obesity and the Energy Homeostasis System

The energy homeostasis system, which includes the melanocortin system and thus the melanocortin receptors, is involved in the regulation of appetite and metabolic rate (also called energy expenditure or total energy expenditure). Obesity is an energy imbalance in which the average energy expenditure of an individual is lower than his or her energy intake (i.e. calories from food intake). The energy homeostasis system in the human body tends to create an energy equilibrium (i.e. energy in=energy out) in the body, to control body weight. However, psychological, pathological, and social factors can force an energy imbalance, generating body-weight fluctuations that depend on the long term ratio of food intake (FIN) and the total energy expenditure (TEE) of the individual. The physiological control of both energy expenditure and energy intake is highly dependent on the neuronal activity in the hypothalamus of the brain. The hypothalamus monitors various molecules (e.g. leptin, insulin and glucose) to determine the energy availability and to accordingly modify the energy expenditure. Experimental data have shown that the energy expenditure can be artificially modulated by stimulating the hypothalamus, in particular the hypothalamic area called the ventromedial hypothalamic nucleus (VMH). Energy expenditure can be increased or decreased by depending on the stimulating factors. Also, depending on the stimulating parameters, an increase in energy expenditure can trigger, among other things, a fat breakdown (lipolysis) which in turn leads to a reduction in appetite. In such a case, the body weight is reduced by the cumulative effects of both the increase in energy expenditure and the reduction of appetite.

The methods described herein may be used to identify, for example, the dorsomedial portion of the VMH, a brain region that includes a significant number of melanocortin receptors. Once the brain region is identified, the target region may be modulated (inhibited or excited) to treat obesity, such as by DBS. Example treatments for obesity are addressed in, for example, U.S. Patent Publication No. 2008/0046012, to Covalin et al., which is incorporated by reference herein in its entirety.

V. Sexual Dysfunction and the Energy Homeostasis System

Brain regions involved in the energy homeostasis system, which includes the melanocortin system and thus the melanocortin receptors, are also involved in the regulation of sexual functions in male and female humans. For example, activation of the melanocortin receptors by pharmacological methods has been shown to increase erectile activity and sexual behavior in rats. The present disclosure relates to methods of identifying brain regions, such as the VMH, where a significant number of melanocortin receptors may be located. More specifically, the target region of interest is the ventrolateral portion of the VMH (v1VMH), where there is a high concentration of MC4 receptors. Once the brain region is identified, the target region may be modulated (inhibited or excited) to treat sexual dysfunction, such as by DBS.

As used herein, sexual functions or dysfunctions may include erectile dysfunction, and female sexual disorder. Erectile dysfunction (ED) is defined as the consistent inability of a male to attain and maintain an erection sufficient for sexual intercourse. The condition is correlated with increasing age, cardiovascular disease, hypertension, diabetes, hyperlipidemia, and smoking. In addition, certain prescription drugs and psychogenic issues may contribute to ED. It is estimated that some degree of ED affects 50% of all men over the age of 40 and that 150 million men worldwide suffer from ED.

Female sexual disorder (FSD) is defined by the American Foundation for Urologic Disease as: "the persistent or recurrent inability to attain or maintain sufficient sexual excitement, causing personal distress. It may be expressed as a lack of subjective excitement or a lack of genital or other somatic responses. FSD consists of four components, hypoactive sexual desire disorder, female sexual arousal disorder (FSAD), dyspareunia or painful intercourse and anorgasmia. To establish a diagnosis of FSD, these components must be associated with personal distress, as determined by the affected woman.

VI. BDNF, Memory, Cognitive Function and the Energy Homeostasis System

As discussed above, brain regions involved in the energy homeostasis system, which includes the melanocortin system and thus the melanocortin receptors, are also involved in memory and cognitive functions (via the expression of BDNF). Brain derived neurotrophic factor (BDNF) is a protein encoded by the BDNF gene. BDNF acts on certain neurons of the central nervous system and the peripheral nervous system, helping to support the survival of existing neurons and encourage the growth and differentiation of new neurons and synapses. In the brain, it is active in the hippocampus, cortex, and basal forebrain. These areas are important in the facilitation of learning, memory, and higher thinking. BDNF itself is also important for long-term memory. BDNF also promotes and enhances the protection and regeneration of neural cells, which may help to reduce cognitive decline). The methods described herein may be used to identify, for example, the dorsomedial portion of the VMH, a brain region that includes a significant number of melanocortin receptors. Once the brain region is identified, the target region may be modulated (inhibited or excited) to modulate expression of BDNF, such as by DBS. Modulating the brain's expression of BDNF is addressed in, for example, U.S. Patent Publication No. 2008/0046012, to Covalin et al., which is incorporated by reference herein in its entirety.

VII. Kits

The present disclosure is also directed to kits that can be used to treat obesity or sexual dysfunction in a patient. The kits can include a device, or component thereof, for performing DBS to a patient. In some embodiments, the kits can further include instructions for targeting a brain region with a targeting agent. In some embodiments, the kits can further include instructions for delivery of deep brain stimulation to a patient. The instructions can include methods described in more detail in the above description.

In various embodiments, the kits include a device or component thereof for treating DBS. The devices can include any commercial DBS system know. For example, one or more of the commercial IPGs (including, but not limited to IPGs described here) may be included in the kit. In alternative embodiments, any leads and/or electrodes may be used separately, or in combination with the IPG to form the system. In certain embodiments, the IPG may be designed to generate frequencies greater than or equal to 1.0 kHz, 2.0 kHz, 3.0 kHz, 4.0 kHz, or 5.0 kHz. The instructions can include methods described in more detail in the above description.

The kits can further include instructions for targeting or identifying a brain region. The instructions provide directions to administer to a patient a first targeting agent that directly or indirectly inhibits a first brain region and to image the first brain region. In some embodiments, the instructions may include directions to administer to a patient a second targeting agent that directly or indirectly inhibits a second brain region and to image the second brain region. The instructions may further provide directions to fuse the first brain image and the second brain image. The instructions can include methods described in more detail in the above description.

The kits can further include instructions for treating obesity or sexual dysfunction, or modulating BDNF expression. In various embodiments, the instructions provide directions for implanting a device into a patient, treating a patient with obesity, and/or for modulating BDNF expression. In other embodiments, the instructions provide directions for implanting a device into a patient, and for treating a patient with sexual dysfunction. The instructions can include any method disclosed herein for modulating the activity of a brain region by applying electrical stimulation to one or more brain regions. The electrical stimulation can have any properties disclosed herein, including frequency, pulse width, amplitude, duration etc. The instructions can include methods described in more detail in the above description.

All references described herein are incorporated by reference in their entirety as if their contents were a part of the present disclosure.

EXAMPLES

The following examples are intended to be non-limiting and illustrative of aspects of the present disclosure.

Example 1

Modulation of the dorsomedial portion of the VMH may be used to treat obesity. The methods disclosed herein may be used to locate the target region during pre-surgical procedures and confirm during surgery that the electrode is in the target region or within range to modulate the target region with a low current, thereby reducing certain side effects.

The patient is positioned in the MRI scanner and fMRI is continuously taken. The level of activity in the hypothalamus is measured using Temporal Clustering Analysis (TCA).

The patient drinks glucose with or without water. As the glucose concentration in the blood rises, the activity in the VMH decreases and therefore the area in the hypothalamus corresponding to the VMH can be identified as the brain region where the activity is decreasing. Alternatively, the patient is administered a direct agonist of, e.g., CB1 receptors. In this case the activity in the VMH increases and thus the VMH can be identified as the brain region where the activity is increasing. Once the VMH is identified, its coordinates are recorded using the best available reference.

After identification of the VMH, the location of the dorsomedial portion of the VMH is functionally determined by administering, e.g., an agonist of the MC3R and/or an agonist of the Leptin receptor and/or OX1R, and/or other as listed in Table 1, via, e.g., intravenous injection. Using an agonist of the MC3R the activity in the dorsomedial portion of the VMH increases and thus the particular area can be identified. Once the dorsomedial portion of the VMH is identified, its coordinates are recorded using the best available reference. In one embodiment, the reference is chosen using a stereotactic frame. In some embodiments, step 1, as described in the immediately preceding paragraph, may not be necessary.

In order to modulate neuronal activity, an electrode is surgically implanted into the dorsomedial portion of the VMH using the coordinates obtained in the steps described in the two immediately preceding paragraphs. In another experiment, a different technique, such as a non-invasive technique, may be used to modulate the neuronal activity. An increase in energy expenditure (EE) is expected and depending on stimulation parameters an increase in lipolysis can be expected, when stimulating the dorsomedial portion of the VMH. Therefore, in order to fine tune the location and/or identification of the brain region, e.g., verify that the modulation is being applied to the desired targeted brain region, at least one of the following is monitored: a) the oxygen consumption (V02), b) the energy expenditure (EE), c) the carbon dioxide production (VCO2), and d) the respiratory quotient (RQ=VCO2/VO2). In some experiments, EE, VO2, VCO2, and RQ is monitored using indirect calorimetry. Using indirect calorimetry, an increase in lipolysis is signaled by a decrease in the RQ.

In other experiments, aside from the MC3Rs, the distribution of the MC4Rs is identified by performing the above-described steps using an appropriate MC4R agonist and the location of the best target determined to be such that a percentage of MC3Rs and a percentage of MC4Rs are modulated.

In other experiments, PET and CT are used. In these experiments the appropriate agonists are made isotopes or paired with isotopes such that they can be detected using PET.

Example 2

Modulation of the ventrolateral portion of the VMH (v1VMH) may be used to treat sexual dysfunction disorders, such as erectile dysfunction and female sexual disorder. The methods disclosed herein may be used to locate the target region during pre-surgical procedures and confirm during surgery that the electrode is in the target region or within range to modulate (i.e. excite) the target region with a low current, thereby reducing certain side effects.

The patient is positioned in the MRI scanner and fMRI is continuously taken. The level of activity in the hypothalamus is measured using Temporal Clustering Analysis (TCA).

The patient drinks glucose with or without water. As the glucose concentration in the blood rises, the activity in the VMH decreases and therefore the area in the hypothalamus corresponding to the VMH can be identified as the brain region where the activity is decreasing. Alternatively, the patient is administered a direct agonist of, e.g., CB1 receptors. In this case the activity in the VMH increases and thus the VMH can be identified as the brain region where the activity is increasing. Once the VMH is identified, its coordinates are recorded using the best available reference. In some embodiments, the reference can be chosen by using a stereotactic frame.

After identification of the VMH, the location of the ventrolateral portion of the VMH is functionally determined by administering, e.g., an agonist or an antagonist of the MC4R, via, e.g., intravenous injection. Using an agonist of the MC4R, the activity in the ventrolateral portion of the VMH increases and thus the particular area can be identified. Using an antagonist of the MC4R, the activity in the ventrolateral portion of the VMH decreases and thus the particular area can be identified. Once the ventrolateral portion of the VMH is identified, its coordinates are recorded using the best available reference. In one embodiment, the reference is chosen using a stereotactic frame. In some embodiments, step 1, as described in the immediately preceding paragraph, may not be necessary.

In order to modulate neuronal activity, an electrode is surgically implanted into the ventrolateral portion of the VMH using the coordinates obtained in the steps described in the two immediately preceding paragraphs. In another experiment, a different technique, such as a non-invasive technique, may be used to modulate the neuronal activity. In order to fine tune the location and/or identification of the brain region, e.g., verify that the modulation is being applied to the desired targeted brain region, signs of sexual arousal may be monitored In some experiments, at least one of the following was also monitored: a) the oxygen consumption (V02), b) the energy expenditure (EE), c) the carbon dioxide production (VCO2), and d) the respiratory quotient (RQ=VCo2/VO2). In some experiments, EE, VO2, VCO2, and RQ were monitored using indirect calorimetry. Using indirect calorimetry, an increase in lipolysis is signaled by a decrease in the RQ.

In other experiments, PET and CT are used. In these experiments the appropriate agonists are made isotopes or paired with isotopes such that they can be detected using PET.

Example 3

Modulation of the Pe or the LHA may be used to modulate feeding behavior. The methods disclosed herein may be used to locate the target region during pre-surgical procedures and confirm during surgery that the electrode is in the target region or within range to modulate the target region with a low current, thereby reducing certain side effects.

The patient is positioned in the MRI scanner and fMRI is continuously taken. The level of activity in the hypothalamus is measured using Temporal Clustering Analysis (TCA).

The location of the Pe and/or LHA is functionally determined by administering, e.g., an agonist or an antagonist of the MOR via, e.g., intracerebral ventricular injection or intravenous injection if the ligand can cross the brain blood barrier. Using an agonist of the MOR, the activity in the Pe and/or LHA increases and thus the particular area can be identified. Using an antagonist of the MOR, the activity in the Pe and/or LHA decreases and thus the particular area can be identified. Once the Pe and/or LHA is identified, its coordinates are recorded using the best available reference. In one embodiment, the reference is chosen using a stereotactic frame.

In order to modulate neuronal activity, an electrode is surgically implanted into the Pe and/or LHA using the coordinates obtained in the step described in the immediately preceding paragraph. In another experiment, a different technique, such as a non-invasive technique, may be used to modulate the neuronal activity.

In other experiments, PET and CT are used. In these experiments the appropriate agonists are made isotopes or paired with isotopes such that they can be detected using PET.

Example 4

Modulation of the dorsomedial portion of the VMH may be used to modulate memory and cognitive performance. The methods disclosed herein may be used to locate the target region during pre-surgical procedures and confirm during surgery that the electrode is in the target region or within range to modulate the target region with a low current, thereby reducing certain side effects. Example treatments for the modulation of memory and cognitive performance are discussed in, for example, U.S. Patent Publication No. 2008/0046012, to Covalin et al., which is incorporated by reference herein in its entirety.

The patient is positioned in the MRI scanner and fMRI is continuously taken. The level of activity in the hypothalamus is measured using Temporal Clustering Analysis (TCA).

The patient drinks glucose with or without water. As the glucose concentration in the blood rises, the activity in the VMH decreases and therefore the area in the hypothalamus corresponding to the VMH can be identified as the brain region where the activity is decreasing. Alternatively, the patient is administered a direct agonist of, e.g., CB1 receptors. In this case the activity in the VMH increases and thus the VMH can be identified as the brain region where the activity is increasing. Once the VMH is identified, its coordinates are recorded using the best available reference. In some embodiments, the reference can be chosen by using a stereotactic frame.

After identification of the VMH, the location of the dorsomedial portion of the VMH is functionally determined by administering, e.g., an agonist of the MC3R and/or an agonist of the Leptin receptor and/or OX1R, and/or other as listed in Table 1, via, e.g., intravenous injection. Using an agonist of the MC3R the activity in the dorsomedial portion of the VMH increases and thus the particular area can be identified. Once the dorsomedial portion of the VMH is identified, its coordinates are recorded using the best available reference. In one embodiment, the reference is chosen using a stereotactic frame. In some embodiments, step 1, as described in the immediately preceding paragraph, may not be necessary.

In order to modulate neuronal activity, an electrode is surgically implanted into the dorsomedial portion of the VMH using the coordinates obtained in the steps described in the two immediately preceding paragraphs. In another experiment, a different technique, such as a non-invasive technique, may be used to modulate the neuronal activity. An increase in energy expenditure (EE) and expected, and, depending on the stimulation parameters, an increase in lipolysis can also be expected when stimulating the dorsomedial portion of the VMH. Therefore, in order to fine tune the location and/or identification of the brain region, e.g., verify that the modulation is being applied to the desired targeted brain region, at least one of the following is monitored: a) the oxygen consumption (V02), b) the energy expenditure (EE), c) the carbon dioxide production (VCO2), and d) the respiratory quotient (RQ=VCO2/VO2). In some experiments, EE, VO2, VCO2, and RQ is monitored using indirect calorimetry. Using indirect calorimetry, an increase in lipolysis is signaled by a decrease in the RQ.

In other experiments, aside from the MC3Rs, the distribution of the MC4Rs is identified by performing the above-described steps using an appropriate MC4R agonist and the location of the best target determined to be such that a percentage of MC3Rs and a percentage of MC4Rs are modulated.

In other experiments, PET and CT are used. In these experiments the appropriate agonists are made isotopes or paired with isotopes such that they can be detected using PET.

Although the present disclosure has been described with reference to preferred embodiments, persons skilled in the art will recognize that changes may be made in form and detail without departing from the spirit and scope of the disclosure.

What is claimed is:

1. A method of identifying a brain region in a patient comprising:
    administering to the patient an effective amount of at least one first targeting agent that binds a target in a first brain region;
    imaging the first brain region thereby creating a first brain image;
    wherein the first brain region is the ventromedial hypothalamic nucleus;
    administering to the patient an effective amount of a second targeting agent that activates or decreases an activity of one of a first and second brain region;
    imaging the second brain region to create a second brain image; and
    identifying the second brain region by fusing the first brain image and the second brain image,
    wherein the target is the MC3 receptor and the first targeting agent is [D-Trp8]-g-MSH and the second targeting agent is PG901.

2. The method of claim 1, wherein the first brain region is a sub-set of the ventromedial hypothalamic nucleus.

3. The method of claim 2, wherein the sub-set of the ventromedial hypothalamic nucleus is at least one of the dorsomedial portion and ventrolateral portion.

4. The method of claim 1, wherein the first targeting agent activates or decreases an activity of the first brain region.

5. The method of claim 1, wherein the imaging step is performed using at least one functional imaging technique and at least one anatomical imaging technique.

6. The method of claim 5, wherein the functional imaging technique is either functional magnetic resonance or positron emission tomography.

7. The method of claim 6 wherein the data from the imaging is analyzed using Temporal Cluster Analysis (CTA).

8. The method of claim 5, wherein the anatomical imaging technique is either magnetic resonance or CT scan.

9. The method of claim 1, further comprising a step of fine-tuning the identification of the first brain region, wherein the step of fine-tuning comprises monitoring at least one of oxygen consumption, energy expenditure, carbon dioxide production or respiratory quotient.

10. The method of claim 1, wherein the second brain region is the ventromedial hypothalamic nucleus.

11. The method of claim 10, wherein the second brain region is a sub-set of the ventromedial hypothalamic nucleus.

12. The method of claim 11, wherein the sub-set of the ventromedial hypothalamic nucleus is at least one of the dorsomedial portion and the ventrolateral portion.

13. The method of claim 1, further comprising a step of fine-tuning the identification of the second brain region, wherein the step of fine-tuning comprises monitoring at least one of oxygen consumption, energy expenditure, carbon dioxide production or respiratory quotient.

14. A method of identifying a brain region in a patient comprising:
- administering to the patient an effective amount of at least one first targeting agent that binds a target in a first brain region;
- imaging the first brain region thereby creating a first brain image, wherein the first brain region is the ventromedial hypothalamic nucleus;
- administering to the patient an effective amount of a second targeting agent that activates or inhibits an activity of one of a first and second brain region;
- imaging the second brain region to create a second brain image; and
- identifying the second brain region by fusing the first brain image and the second brain image,
- wherein the target is the MC4 receptor and the first targeting agent is RY764 and the second targeting agent is MCLO129.

15. The method of claim 14, wherein the first brain region is a sub-set of the ventromedial hypothalamic nucleus.

16. The method of claim 15, wherein the sub-set of the ventromedial hypothalamic nucleus is at least one of the dorsomedial portion and ventrolateral portion.

17. The method of claim 14, wherein the first targeting agent activates or inhibits an activity of the first brain region.

18. The method of claim 14, wherein the imaging step is performed using at least one functional imaging technique and at least one anatomical imaging technique.

19. The method of claim 18, wherein the functional imaging technique is either functional magnetic resonance or positron emission tomography.

20. The method of claim 19 wherein the data from the imaging is analyzed using Temporal Cluster Analysis (CTA).

21. The method of claim 18, wherein the anatomical imaging technique is either magnetic resonance or CT scan.

22. The method of claim 14, further comprising a step of fine-tuning the identification of the first brain region, wherein the step of fine-tuning comprises monitoring at least one of oxygen consumption, energy expenditure, carbon dioxide production or respiratory quotient.

23. The method of claim 14, wherein the second brain region is the ventromedial hypothalamic nucleus.

24. The method of claim 23, wherein the second brain region is a sub-set of the ventromedial hypothalamic nucleus.

25. The method of claim 24, wherein the sub-set of the ventromedial hypothalamic nucleus is at least one of the dorsomedial portion and the ventrolateral portion.

26. The method of claim 14, further comprising a step of fine-tuning the identification of the second brain region, wherein the step of fine-tuning comprises monitoring at least one of oxygen consumption, energy expenditure, carbon dioxide production or respiratory quotient.

* * * * *